(12) United States Patent
Murray et al.

(10) Patent No.: US 10,293,122 B2
(45) Date of Patent: May 21, 2019

(54) ENDOLUMINAL INTRODUCER WITH CONTAMINATION AVOIDANCE

(71) Applicant: Novadaq Technologies ULC, Burnaby (CA)

(72) Inventors: Gavin Michael Murray, Vancouver (CA); Gregory Vincent Browne, Vancouver (CA)

(73) Assignee: NOVADAQ TECHNOLOGIES ULC, Burnaby (CA)

( * ) Notice: Subject to any disclaimer, the term of this patent is extended or adjusted under 35 U.S.C. 154(b) by 55 days.

(21) Appl. No.: 15/073,259

(22) Filed: Mar. 17, 2016

(65) Prior Publication Data

US 2017/0266398 A1  Sep. 21, 2017

(51) Int. Cl.
*A61M 37/00* (2006.01)
*A61M 13/00* (2006.01)

(52) U.S. Cl.
CPC ......... *A61M 13/00* (2013.01); *A61M 2202/02* (2013.01); *A61M 2205/33* (2013.01); *A61M 2205/582* (2013.01)

(58) Field of Classification Search
CPC .............. A61M 13/00; A61M 2202/02; A61M 2205/33; A61M 2205/582; A61M 25/0102; A61M 2039/0279
See application file for complete search history.

(56) References Cited

U.S. PATENT DOCUMENTS 3,215,029 A   11/1965  Woodcock
3,257,902 A   6/1966   Hopkins
3,971,068 A   7/1976   Gerhardt et al.
(Continued)

FOREIGN PATENT DOCUMENTS

CA   2404600 A1   10/2001
CN   200987662 Y  12/2007
(Continued)

OTHER PUBLICATIONS

Alfano, R.R. et al. (Oct. 1987). "Fluorescence Spectra From Cancerous and Normal Human Breast and Lung Tissues," *IEEE Journal of Quantum Electronics* QE-23(10):1806-1811.
(Continued)

*Primary Examiner* — Rebecca E Eisenberg
(74) *Attorney, Agent, or Firm* — Morrison & Foerster LLP

(57) ABSTRACT

Described herein are introducer devices and methods for using an introducer device to facilitate passing an endoluminal instrument to a target region of a body cavity. An introducer device may include a tubular member having an inner wall that defines a channel configured to receive the endoluminal instrument and a plurality of projections disposed in the channel at perimetrically spaced apart locations around the inner wall, where the projections extend inward and are configured to offset the endoluminal instrument from the inner wall, thereby creating a space between the endoluminal instrument and the inner wall. A method for using an introducer device may include passing the endoluminal instrument to a first instrument insertion depth within the introducer device, advancing the introducer device in the body cavity, and advancing the endoluminal instrument to a second instrument insertion depth within the introducer device.

21 Claims, 12 Drawing Sheets

(56) References Cited

U.S. PATENT DOCUMENTS

| | | |
|---|---|---|
| 4,037,866 A | 7/1977 | Price |
| 4,066,330 A | 1/1978 | Jones |
| 4,115,812 A | 9/1978 | Akatsu |
| 4,149,190 A | 4/1979 | Wessler et al. |
| 4,200,801 A | 4/1980 | Schuresko |
| 4,318,395 A | 3/1982 | Tawara |
| 4,355,325 A | 10/1982 | Nakamura et al. |
| 4,378,571 A | 3/1983 | Handy |
| 4,449,535 A | 5/1984 | Renault |
| 4,471,766 A | 9/1984 | Terayama |
| 4,532,918 A | 8/1985 | Wheeler |
| 4,556,057 A | 12/1985 | Hiruma et al. |
| 4,611,888 A | 9/1986 | Prenovitz et al. |
| 4,638,365 A | 1/1987 | Kato |
| 4,655,557 A | 4/1987 | Takahashi |
| 4,660,982 A | 4/1987 | Okada |
| 4,768,513 A | 9/1988 | Suzuki |
| 4,786,813 A | 11/1988 | Svanberg et al. |
| 4,821,117 A | 4/1989 | Sekiguchi |
| 4,837,625 A | 6/1989 | Douziech et al. |
| 4,856,495 A | 8/1989 | Tohjoh et al. |
| 4,895,145 A | 1/1990 | Joffe |
| 4,917,457 A | 4/1990 | Iizuka |
| 4,930,516 A | 6/1990 | Alfano et al. |
| 4,951,135 A | 8/1990 | Sasagawa et al. |
| 4,954,897 A | 9/1990 | Ejima et al. |
| 4,974,936 A | 12/1990 | Ams et al. |
| 5,001,556 A | 3/1991 | Nakamura et al. |
| 5,005,960 A | 4/1991 | Heimbeck |
| 5,007,408 A | 4/1991 | Ieoka |
| 5,034,888 A | 7/1991 | Uehara et al. |
| 5,134,662 A | 7/1992 | Bacus et al. |
| 5,142,410 A | 8/1992 | Ono et al. |
| 5,165,079 A | 11/1992 | Schulz-Hennig |
| 5,205,280 A | 4/1993 | Dennison, Jr. et al. |
| 5,206,759 A | 4/1993 | Ono et al. |
| 5,214,503 A | 5/1993 | Chiu et al. |
| 5,225,883 A | 7/1993 | Carter et al. |
| 5,255,087 A | 10/1993 | Nakamura et al. |
| 5,278,642 A | 1/1994 | Danna et al. |
| 5,305,759 A | 4/1994 | Kaneko et al. |
| 5,334,191 A | 8/1994 | Poppas et al. |
| 5,365,057 A | 11/1994 | Morley et al. |
| 5,371,355 A | 12/1994 | Wodecki |
| 5,377,686 A | 1/1995 | O'Rourke et al. |
| 5,379,756 A | 1/1995 | Pileski et al. |
| 5,403,264 A * | 4/1995 | Wohlers ............ A61B 17/00234 600/101 |
| 5,408,263 A | 4/1995 | Kikuchi et al. |
| 5,410,363 A | 4/1995 | Capen et al. |
| 5,419,323 A | 5/1995 | Kittrell et al. |
| 5,420,628 A | 5/1995 | Poulsen et al. |
| 5,421,337 A | 6/1995 | Richards-Kortum et al. |
| 5,424,841 A | 6/1995 | Van Gelder et al. |
| 5,430,476 A | 7/1995 | Hafele et al. |
| 5,460,166 A | 10/1995 | Yabe et al. |
| 5,461,509 A | 10/1995 | Canzek |
| 5,485,203 A | 1/1996 | Nakamura et al. |
| 5,490,015 A | 2/1996 | Umeyama et al. |
| 5,507,287 A | 4/1996 | Palcic et al. |
| 5,536,236 A | 7/1996 | Yabe et al. |
| 5,576,882 A | 11/1996 | Kanamori |
| 5,585,846 A | 12/1996 | Kim |
| 5,590,660 A | 1/1997 | MacAulay et al. |
| 5,596,654 A | 1/1997 | Tanaka |
| 5,646,680 A | 7/1997 | Yajima |
| 5,647,368 A | 7/1997 | Zeng et al. |
| 5,647,840 A | 7/1997 | D'Amelio et al. |
| 5,667,472 A | 9/1997 | Finn et al. |
| 5,684,629 A | 11/1997 | Leiner |
| 5,695,049 A | 12/1997 | Bauman |
| 5,697,373 A | 12/1997 | Richards-Kortum et al. |
| 5,697,888 A | 12/1997 | Kobayashi et al. |
| 5,713,364 A | 2/1998 | DeBaryshe et al. |
| 5,722,962 A | 3/1998 | Garcia |
| 5,749,830 A | 5/1998 | Kaneko et al. |
| 5,772,355 A | 6/1998 | Ross et al. |
| 5,772,580 A | 6/1998 | Utsui et al. |
| 5,827,190 A | 10/1998 | Palcic et al. |
| 5,833,617 A | 11/1998 | Hayashi |
| 5,852,498 A | 12/1998 | Youvan et al. |
| 5,891,016 A | 4/1999 | Utsui et al. |
| 5,892,625 A | 4/1999 | Heimer |
| 5,897,269 A | 4/1999 | Ross et al. |
| 5,910,816 A | 6/1999 | Fontenot et al. |
| 5,941,815 A | 8/1999 | Chang |
| 5,952,768 A | 9/1999 | Strok et al. |
| 5,971,918 A | 10/1999 | Zanger |
| 5,976,146 A | 11/1999 | Ogawa et al. |
| 5,984,861 A | 11/1999 | Crowley |
| 5,986,271 A | 11/1999 | Lazarev et al. |
| 5,986,642 A | 11/1999 | Lazarev et al. |
| 5,990,996 A | 11/1999 | Sharp |
| 5,999,240 A | 12/1999 | Sharp et al. |
| 6,002,137 A | 12/1999 | Hayashi |
| 6,004,263 A | 12/1999 | Nakaichi et al. |
| 6,008,889 A | 12/1999 | Zeng et al. |
| 6,021,344 A | 2/2000 | Lui et al. |
| 6,028,622 A | 2/2000 | Suzuki |
| 6,030,339 A | 2/2000 | Tatsuno et al. |
| 6,059,719 A | 5/2000 | Yamamoto et al. |
| 6,059,720 A | 5/2000 | Furusawa et al. |
| 6,061,591 A | 5/2000 | Freitag et al. |
| 6,069,689 A | 5/2000 | Zeng et al. |
| 6,070,096 A | 5/2000 | Hayashi |
| 6,095,982 A | 8/2000 | Richards-Kortum et al. |
| 6,099,466 A | 8/2000 | Sano et al. |
| 6,110,103 A | 8/2000 | Donofrio |
| 6,110,106 A | 8/2000 | MacKinnon et al. |
| 6,120,435 A | 9/2000 | Eino |
| 6,148,227 A | 11/2000 | Wagnieres et al. |
| 6,161,035 A | 12/2000 | Furusawa |
| 6,166,496 A | 12/2000 | Lys et al. |
| 6,192,267 B1 | 2/2001 | Scherninski et al. |
| 6,212,425 B1 | 4/2001 | Irion et al. |
| 6,258,576 B1 | 7/2001 | Richards-Kortum et al. |
| 6,280,378 B1 | 8/2001 | Kazuhiro et al. |
| 6,293,911 B1 | 9/2001 | Imaizumi et al. |
| 6,332,092 B1 | 12/2001 | Deckert et al. |
| 6,347,010 B1 | 2/2002 | Chen et al. |
| 6,351,663 B1 | 2/2002 | Flower et al. |
| 6,364,829 B1 | 4/2002 | Fulghum |
| 6,364,831 B1 | 4/2002 | Crowley |
| 6,388,702 B1 | 5/2002 | Konomura et al. |
| 6,419,628 B1 | 7/2002 | Rudischhauser et al. |
| 6,422,994 B1 | 7/2002 | Kaneko et al. |
| 6,433,102 B1 | 8/2002 | Suzuki et al. |
| 6,443,976 B1 | 9/2002 | Flower et al. |
| 6,461,330 B1 | 10/2002 | Miyagi |
| 6,490,085 B1 | 12/2002 | Zobel |
| 6,526,213 B1 | 2/2003 | Ilenda et al. |
| 6,527,709 B2 | 3/2003 | Matsumoto |
| 6,529,768 B1 | 3/2003 | Hakamata |
| 6,537,211 B1 | 3/2003 | Wang et al. |
| 6,544,102 B2 | 4/2003 | Schafer et al. |
| 6,571,119 B2 | 5/2003 | Hayashi |
| 6,603,552 B1 | 8/2003 | Cline et al. |
| 6,639,664 B2 | 10/2003 | Haan et al. |
| 6,772,003 B2 | 8/2004 | Kaneko et al. |
| 6,773,392 B2 | 8/2004 | Kikuchi et al. |
| 6,786,865 B2 | 9/2004 | Dhindsa |
| 6,821,245 B2 | 11/2004 | Cline et al. |
| 6,853,485 B2 | 2/2005 | Hoogland |
| 6,898,458 B2 | 5/2005 | Zeng et al. |
| 6,899,675 B2 | 5/2005 | Cline et al. |
| 6,907,527 B1 | 6/2005 | Wu |
| 6,911,005 B2 | 6/2005 | Ouchi et al. |
| 6,915,154 B1 | 7/2005 | Docherty et al. |
| 6,944,493 B2 | 9/2005 | Alam et al. |
| 6,958,035 B2 | 10/2005 | Friedman et al. |
| 6,960,165 B2 | 11/2005 | Ueno et al. |
| 7,033,314 B2 | 4/2006 | Kamrava et al. |
| 7,043,291 B2 | 5/2006 | Sendai |
| 7,235,045 B2 | 6/2007 | Wang et al. |

(56) References Cited

U.S. PATENT DOCUMENTS

| | | | |
|---|---|---|---|
| 7,236,815 B2 | 6/2007 | Richards-Kortum et al. |
| 7,324,674 B2 | 1/2008 | Ozawa et al. |
| 7,341,557 B2 | 3/2008 | Cline et al. |
| 7,364,574 B2 | 4/2008 | Flower |
| 7,385,772 B2 | 6/2008 | Forkey et al. |
| 7,704,206 B2 | 4/2010 | Suzuki et al. |
| 7,722,534 B2 | 5/2010 | Cline et al. |
| 7,724,430 B2 | 5/2010 | Kasai |
| 7,733,583 B2 | 6/2010 | Fujiwara |
| 7,733,584 B2 | 6/2010 | Kazakevich |
| 7,798,955 B2 | 9/2010 | Ishihara et al. |
| 7,862,504 B2 | 1/2011 | Kura et al. |
| 7,918,559 B2 | 4/2011 | Tesar |
| 8,408,269 B2 | 4/2013 | Fengler et al. |
| 8,506,555 B2 | 8/2013 | Ruiz Morales |
| 8,630,698 B2 | 1/2014 | Fengler et al. |
| 8,780,445 B2 | 7/2014 | Inoue |
| 8,961,403 B2 | 2/2015 | Cline et al. |
| 9,241,615 B2 | 1/2016 | Yoshida et al. |
| 9,386,909 B2 | 7/2016 | Fengler et al. |
| 9,877,654 B2 | 1/2018 | Tesar |
| 9,918,619 B2 | 3/2018 | Tesar |
| 9,968,244 B2 | 5/2018 | Cline et al. |
| 2001/0016679 A1 | 8/2001 | Futatsugi et al. |
| 2002/0001080 A1 | 1/2002 | Miller et al. |
| 2002/0057501 A1 | 5/2002 | Lei |
| 2002/0072736 A1 | 6/2002 | Tierney et al. |
| 2002/0087047 A1 | 7/2002 | Remijan et al. |
| 2002/0103439 A1 | 8/2002 | Zeng et al. |
| 2002/0138008 A1 | 9/2002 | Tsujita et al. |
| 2002/0161283 A1 | 10/2002 | Sendai |
| 2002/0161284 A1 | 10/2002 | Tanaka |
| 2002/0175993 A1 | 11/2002 | Ueno et al. |
| 2002/0177778 A1 | 11/2002 | Averback et al. |
| 2002/0186478 A1 | 12/2002 | Watanabe et al. |
| 2003/0002036 A1 | 1/2003 | Haan et al. |
| 2003/0042493 A1 | 3/2003 | Kazakevich |
| 2003/0153811 A1 | 8/2003 | Muckner |
| 2003/0219383 A1 | 11/2003 | Weissleder et al. |
| 2003/0229270 A1 | 12/2003 | Suzuki et al. |
| 2004/0010183 A1 | 1/2004 | Dhindsa |
| 2004/0021859 A1 | 2/2004 | Cunningham |
| 2004/0037454 A1 | 2/2004 | Ozawa et al. |
| 2004/0046865 A1 | 3/2004 | Ueno et al. |
| 2004/0054255 A1 | 3/2004 | Pilgrim et al. |
| 2004/0125445 A1 | 7/2004 | Hoogland |
| 2004/0133073 A1 | 7/2004 | Berci et al. |
| 2004/0142485 A1 | 7/2004 | Flower et al. |
| 2004/0143162 A1 | 7/2004 | Krattiger et al. |
| 2004/0148141 A1 | 7/2004 | Tsujita et al. |
| 2004/0156124 A1 | 8/2004 | Okada |
| 2004/0186383 A1 | 9/2004 | Rava et al. |
| 2004/0204671 A1 | 10/2004 | Stubbs et al. |
| 2004/0218115 A1 | 11/2004 | Kawana et al. |
| 2005/0027166 A1 | 2/2005 | Matsumoto et al. |
| 2005/0075575 A1 | 4/2005 | Vo-Dinh |
| 2005/0096505 A1 | 5/2005 | Imaizumi et al. |
| 2005/0143627 A1 | 6/2005 | Cline et al. |
| 2005/0152027 A1 | 7/2005 | Armstrong et al. |
| 2005/0154319 A1 | 7/2005 | Cline et al. |
| 2005/0182291 A1 | 8/2005 | Hirata |
| 2005/0256373 A1 | 11/2005 | Bar-Or et al. |
| 2005/0267331 A1 | 12/2005 | Secrest et al. |
| 2005/0275057 A1 | 12/2005 | Breen et al. |
| 2005/0288622 A1* | 12/2005 | Albrecht ............ A61B 17/3417 604/23 |
| 2006/0017913 A1 | 1/2006 | Kawamata et al. |
| 2006/0089554 A1 | 4/2006 | Ishihara et al. |
| 2006/0146322 A1 | 7/2006 | Komachi et al. |
| 2006/0211915 A1 | 9/2006 | Takeuchi et al. |
| 2006/0217594 A1 | 9/2006 | Ferguson |
| 2006/0239921 A1 | 10/2006 | Mangat et al. |
| 2006/0241496 A1 | 10/2006 | Fengler et al. |
| 2006/0258910 A1 | 11/2006 | Stefanchik et al. |
| 2008/0021274 A1 | 1/2008 | Bayer et al. |
| 2008/0081948 A1 | 4/2008 | Weisenburgh et al. |
| 2008/0239070 A1 | 10/2008 | Westwick et al. |
| 2008/0273247 A1 | 11/2008 | Kazakevich |
| 2009/0012361 A1 | 1/2009 | MacKinnon et al. |
| 2009/0209813 A1 | 8/2009 | Lubowski et al. |
| 2009/0290236 A1 | 11/2009 | Wang et al. |
| 2009/0303317 A1 | 12/2009 | Tesar |
| 2010/0081988 A1 | 4/2010 | Kahle et al. |
| 2010/0106235 A1* | 4/2010 | Kariniemi ............... A61F 2/07 623/1.11 |
| 2010/0125164 A1 | 5/2010 | LaBombard |
| 2010/0168588 A1 | 7/2010 | Matsumoto et al. |
| 2010/0198010 A1 | 8/2010 | Cline et al. |
| 2010/0277817 A1 | 11/2010 | Durell |
| 2011/0230719 A1 | 9/2011 | Katakura et al. |
| 2011/0249323 A1 | 10/2011 | Tesar et al. |
| 2012/0316394 A1 | 12/2012 | Yoshida et al. |
| 2013/0184591 A1 | 7/2013 | Tesar |
| 2013/0194667 A1 | 8/2013 | Inoue |
| 2014/0187859 A1* | 7/2014 | Leeuw ............... A61B 17/3474 600/114 |
| 2014/0194687 A1 | 7/2014 | Fengler et al. |
| 2014/0343362 A1 | 11/2014 | Tesar |
| 2015/0230698 A1 | 8/2015 | Cline et al. |
| 2016/0270640 A1 | 9/2016 | Fengler et al. |
| 2018/0168455 A1 | 6/2018 | Tesar |

FOREIGN PATENT DOCUMENTS

| | | |
|---|---|---|
| CN | 101115995 A | 1/2008 |
| CN | 201048936 Y | 4/2008 |
| CN | 201085616 Y | 7/2008 |
| CN | 102004309 A | 4/2011 |
| CN | 103091829 A | 5/2013 |
| DE | 195 35 114 A1 | 3/1996 |
| DE | 196 08 027 A1 | 9/1996 |
| EP | 0 512 965 A1 | 11/1992 |
| EP | 0 672 379 A1 | 9/1995 |
| EP | 0 774 685 A2 | 5/1997 |
| EP | 0 774 865 A2 | 5/1997 |
| EP | 0 792 618 A1 | 9/1997 |
| EP | 1 232 764 A1 | 8/2002 |
| EP | 1 374 755 A1 | 1/2004 |
| EP | 1 883 337 A1 | 2/2008 |
| EP | 2 028 519 A2 | 2/2009 |
| EP | 2 051 603 A1 | 4/2009 |
| EP | 2 106 739 A2 | 10/2009 |
| FR | 2 671 405 A1 | 7/1992 |
| JP | S60-246733 A | 12/1985 |
| JP | S61-159936 A | 7/1986 |
| JP | H01-135349 A | 5/1989 |
| JP | H02-272513 A | 11/1990 |
| JP | 03-97439 A | 4/1991 |
| JP | 03-97441 A | 4/1991 |
| JP | 03-97442 A | 4/1991 |
| JP | H03-136630 A | 6/1991 |
| JP | H05-005101 U | 1/1993 |
| JP | H05-115435 A | 5/1993 |
| JP | 6-63164 A | 3/1994 |
| JP | H06-094989 A | 4/1994 |
| JP | 06-125911 A | 5/1994 |
| JP | H06-068702 U | 9/1994 |
| JP | H07-155285 A | 6/1995 |
| JP | H07-155286 A | 6/1995 |
| JP | H07-155290 A | 6/1995 |
| JP | H07-155291 A | 6/1995 |
| JP | H07-155292 A | 6/1995 |
| JP | H07-184832 A | 7/1995 |
| JP | H07-204156 A | 8/1995 |
| JP | H07-222712 A | 8/1995 |
| JP | H07-250804 A | 10/1995 |
| JP | H07-250812 A | 10/1995 |
| JP | H07-327913 A | 12/1995 |
| JP | H08-056894 A | 3/1996 |
| JP | H08-094928 A | 4/1996 |
| JP | H08-126605 A | 5/1996 |
| JP | 08-140928 A | 6/1996 |
| JP | 08-140929 A | 6/1996 |
| JP | H08-168465 A | 7/1996 |

(56) References Cited

FOREIGN PATENT DOCUMENTS

| | | |
|---|---|---|
| JP | H08-224208 A | 9/1996 |
| JP | H08-224209 A | 9/1996 |
| JP | H08-224210 A | 9/1996 |
| JP | H08-224240 A | 9/1996 |
| JP | H08-228998 A | 9/1996 |
| JP | H08-252218 A | 10/1996 |
| JP | 09-66023 A | 3/1997 |
| JP | 09-070384 A | 3/1997 |
| JP | H10-127563 A | 5/1998 |
| JP | H10-151104 A | 6/1998 |
| JP | H10-192297 A | 7/1998 |
| JP | 10-201707 A2 | 8/1998 |
| JP | 10-225427 A2 | 8/1998 |
| JP | H10-201700 A | 8/1998 |
| JP | H10-225426 A | 8/1998 |
| JP | H10-243915 A | 9/1998 |
| JP | H10-243920 A | 9/1998 |
| JP | H10-262907 A | 10/1998 |
| JP | H10-308114 A | 11/1998 |
| JP | H10-309281 A | 11/1998 |
| JP | H10-309282 A | 11/1998 |
| JP | H10-328129 A | 12/1998 |
| JP | 11-047079 A | 2/1999 |
| JP | 11-089789 A2 | 4/1999 |
| JP | H11-104059 A | 4/1999 |
| JP | H11-104060 A | 4/1999 |
| JP | H11-104061 A | 4/1999 |
| JP | H11-104070 A | 4/1999 |
| JP | H11-113839 A | 4/1999 |
| JP | H11-155812 A | 6/1999 |
| JP | H11-244220 A | 9/1999 |
| JP | H11-332819 A | 12/1999 |
| JP | 2000-504968 A | 4/2000 |
| JP | 2000-245693 A | 9/2000 |
| JP | 2000-287915 A | 10/2000 |
| JP | 2000-354583 A | 12/2000 |
| JP | 2001-212245 A | 8/2001 |
| JP | 2002-244122 A | 8/2002 |
| JP | 2004-024611 A | 1/2004 |
| JP | 2004-057520 A | 2/2004 |
| JP | 2004-094043 A | 3/2004 |
| JP | 2004-163902 A | 6/2004 |
| JP | 2004-247156 A | 9/2004 |
| JP | 2004-292722 A | 10/2004 |
| JP | 2005-010315 A | 1/2005 |
| JP | 2005-058618 A2 | 3/2005 |
| JP | 2005-058619 A2 | 3/2005 |
| JP | 2005-058620 A2 | 3/2005 |
| JP | 2005-080819 A2 | 3/2005 |
| JP | 2005-081079 A2 | 3/2005 |
| JP | 2005-292404 A | 10/2005 |
| JP | 2007-143624 A | 6/2007 |
| JP | 2008-511341 A | 4/2008 |
| JP | 2009-048085 A | 3/2009 |
| JP | 2009-247566 A | 10/2009 |
| JP | 2010-526342 A | 7/2010 |
| JP | 2012-050618 A | 3/2012 |
| JP | 5089168 B2 | 12/2012 |
| RU | 2412800 C2 | 2/2011 |
| WO | WO-1993/04648 A1 | 3/1993 |
| WO | WO-1995/26673 A2 | 10/1995 |
| WO | WO-1998/24360 A1 | 6/1998 |
| WO | WO-1999/01749 A1 | 1/1999 |
| WO | WO-1999/53832 A1 | 10/1999 |
| WO | WO-2000/06013 A1 | 2/2000 |
| WO | WO-2000/42910 A1 | 7/2000 |
| WO | WO-2000/54652 A1 | 9/2000 |
| WO | WO-2002/07587 A2 | 1/2002 |
| WO | WO-2003/059159 A2 | 7/2003 |
| WO | WO-2003/059159 A8 | 7/2003 |
| WO | WO-2005/110196 A1 | 11/2005 |
| WO | WO-2006/116634 A2 | 11/2006 |
| WO | WO-2006/116847 A1 | 11/2006 |
| WO | WO-2006/119349 A2 | 11/2006 |
| WO | WO-2008/011722 A1 | 1/2008 |
| WO | WO-2013/021704 A1 | 2/2013 |
| WO | WO-2014/199236 A2 | 12/2014 |

OTHER PUBLICATIONS

Andersson-Engels, S. et al. (1989). "Tissue Diagnostics Using Laser-Induced Fluorescence," *Ber. Bunsenges Physical Chemistry* 93:335-342.

Arregui, M.E. et al. (1996). "Visualization," Chapter 35 in *Principles of Lacroscopic Surgery*, Springer-Verlag New York, NY, pp. 767-794.

Bennett J.M. et al. (Feb. 1965). "Infrared Reflectance and Emittance of Silver and Gold Evaporated in Ultrahigh Vacuum," *Applied Optics* 4(2):221-224.

Bhunchet, E. et al. (2002). "Fluorescein Electronic Endoscopy: A Novel Method for Detection of Early Stage Gastric Cancer Not Evident to Routine Endoscopy," *Gastrointestinal Endoscopy* 55(4):562-571.

Hung, J. et al.(1991). "Autofluorescence of Normal and Malignant Bronchial Tissue," *Lasers in Surgery and Medicine* 11:99-105.

Orfanidis, S. J. (Jun. 21, 2004) "Multilayer Structures," Chapter 5 in *Electromagnetic Waves and Antennas*, published by Sophocoles; <http://www.ece.rutgers.edu/~orfanidi/ewa>; twenty five pages.

O'Shea, D. et al.(1995). "Aberration Curves in Lens Design," Chapter 33 in *Handbook of Optics Fundamentals, Techniques and Design*, McGraw-Hill, Inc., pp. 33.1-33.6.

Schott AG's Catalog for Optical Glasses. (Feb. 2016). "As the source of the SCHOTT Table."

Sherwinter, D.A. (Aug. 2013, e-published on Oct. 11, 2012). "A Novel Adaptor Converts a Laparoscope Into a high-Definition Rigid Sigmoidoscope," *Surgical Innovation* 20(4):411-413.

Tomkinson, T.H. et al. (Dec. 1, 1996). "Rigid Endoscopic Relay Systems: A Comparative Study," *Applied Optics* 35:6674-6683.

Canadian Office Action dated Dec. 30, 2015, for Canadian Patent Application No. 2,896,267, filed Sep. 22, 2014, four pages.

Canadian Office Action dated Feb. 5, 2018 for Canadian Patent Application No. 2911861 filed on Nov. 16, 2015, four pages.

Canadian Office Action dated Nov. 29, 2016, for Canadian Patent Application No. 2,896,267, filed Sep. 22, 2014, four pages.

Canadian Office Action dated Jan. 4, 2017 for Canadian Application No. 2,911,861, filed on May 15, 2014, four pages.

Chinese First Office Action dated Aug. 3, 2016 for Chinese Application No. 201380073686.0 filed Dec. 24, 2013, eight pages.

Chinese First Office Action dated Nov. 2, 2016 for Chinese Application No. 201480027537.5 filed May 15, 2014, 17 pages.

Chinese Office Action dated Aug. 21, 2017, for Chinese Application No. 201480027537.5, filed on May 15, 2014, seventeen pages.

Chinese Second Office Action dated Mar. 9, 2017, for Chinese Application No. 201380073686.0, filed on Dec. 24, 2013, nineteen pages.

European Communication pursuant to Rules 70(2) and 70a(2) EPC dated Aug. 4, 2016 for European Application No. 13871081.9 filed on Dec. 24, 2013, one page.

European Extended Search Report dated Dec. 16, 2016 for EP Application No. 14810752.7 filed on Sep. 8, 2016, eight pages.

European Office Action dated Nov. 19, 2015, for EP Application No. 07 785 001.4, filed on Jul. 30, 2007, four pages.

European Supplementary Search Report dated Oct. 9, 2013, for European Patent Application No. 06721854.5 filed May 4, 2005, six pages.

European Supplementary Search Report dated Jan. 24, 2012 for EP Application No. 07 785 001.4, filed on Jul. 30, 2007, seven pages.

Extended European Search Report dated Jul. 18, 2016 for European Application No. 13871081.9 filed on Dec. 24, 2013, seven pages.

International Preliminary Report on Patentability dated Feb. 3, 2009, for International Application No. PCT/CA2007/001335 filed Jul. 30, 2007, five pages.

International Preliminary Report on Patentability dated Nov. 6, 2007, for International Application No. PCT/CA2006/000669 filed Apr. 27, 2006, nine pages.

(56) References Cited

OTHER PUBLICATIONS

International Search Report and Written Opinion dated Sep. 22, 2014, for International Application No. PCT/IB2013/003243 filed on Dec. 24, 2013, six pages.
International Search Report dated Aug. 3, 2006, for International Application No. PCT/CA2006/000669, filed on Apr. 27, 2006, three pages.
International Search Report dated Dec. 7, 2007, for International Application No. PCT/CA2007/001335, filed Jul. 30, 2007, two pages.
International Search Report dated Feb. 26, 2008 for International Application No. PCT/US07/061810 filed Feb. 7, 2007, two pages.
International Search Report dated Jan. 21, 2002, for International Application No. PCT/US2001/022198, filed on Jul. 13, 2001, three pages.
Japanese Final Office Action dated Aug. 2, 2013, for Japanese Patent Application No. 2008-509275, filed on Apr. 27, 2006, four pages.
Japanese Notice of Allowance dated Sep. 4, 2017 for Japanese Patent Application No. 2016-513460, filed on May 15, 2014, six pages.
Japanese Office Action dated Feb. 17, 2012, for Japanese Patent Application No. 2008-509275, filed on Apr. 27, 2006, six pages.
Japanese Office Action dated Jul. 4, 2016 for Japanese Patent Application No. 2015-550160 filed Dec. 24, 2013, ten pages.
Japanese Office Action dated Nov. 11, 2011, for Japanese Patent Application No. 2009-521077, filed on Jul. 30, 2007, four pages.
Japanese Office Action dated Dec. 5, 2016 for Japanese Patent Application No. 2016-513460, filed on May 15, 2014, nine pages.
Japanese Office Action dated Mar. 3, 2017 for Japanese Patent Application No. 2015-550160, filed on Jun. 24, 2015, nine pages.
Japanese Office Action dated Sep. 14, 2012, for Japanese Patent Application No. 2008-509275, filed on Apr. 27, 2006, seven pages.
Japanese Office Action dated Sep. 19, 2014, for Japanese Patent Application No. 2013-246636, filed on Apr. 27, 2006, six pages.
Korean Final Office Action dated Feb. 13, 2017, for Korean Patent Application No. 2015-7019659, filed on Jul. 20, 2015, twelve pages.
Korean Notice of Allowance dated Aug. 14, 2017, for Korean Application No. 10-2015-7035138, filed on Dec. 10, 2015, three pages.
Korean Office Action dated Jan. 6, 2017 for Korean Patent Application No. 10-2015-7035138 filed on Dec. 10, 2015, ten pages.
Korean Office Action dated Jul. 15, 2016 for Korean Patent Application No. 10-2015-7019659 filed Dec. 24, 2013, twelve pages.
Russian Office Action dated Dec. 29, 2016, for Russian Application No. 2015124802, filed on Dec. 24, 2013, thirteen pages.
U.S. Final Office Action dated Aug. 8, 2016 for U.S. Appl. No. 14/278,833, filed May 15, 2014, seven pages.
U.S. Final Office Action dated Dec. 7, 2015 for U.S. Appl. No. 13/585,824, filed Aug. 14, 2012, ten pages.
U.S. Final Office Action dated Feb. 14, 2012, for U.S. Appl. No. 12/278,740, filed Dec. 10, 2008, 6 pages.
U.S. Final Office Action dated Jan. 23, 2017 for U.S. Appl. No. 14/140,370, filed Dec. 24, 2013, twelve pages.
U.S. Final Office Action dated Jul. 13, 2014 for U.S. Appl. No. 13/585,824, filed Aug. 14, 2012, nine pages.
U.S. Final Office Action dated Mar. 3, 2016 for U.S. Appl. No. 14/140,370, filed Dec. 24, 2013, ten pages.
U.S. Final Office Action dated May 19, 2017, for U.S. Appl. No. 14/975,707, filed Dec. 18, 2015, six pages.
U.S. Final Office Action dated Oct. 6, 2016 for U.S. Appl. No. 14/629,473, filed Feb. 23, 2015, seventeen pages.
U.S. Final Office Action dated Jul. 23, 2008, for U.S. Appl.No. 11/122,267, filed May 4, 2005, six pages.
U.S. Final Office Action dated Jun. 18, 2015, for U.S. Appl. No. 14/154,177, filed Jan. 13, 2014, eight pages.
U.S. Final Office Action dated Jun. 5, 2014, for U.S. Appl. No. 12/761,462, filed Apr. 16, 2010, fourteen pages.
U.S. Final Office Action dated May 11, 2011, for U.S. Appl. No. 11/412,715, filed Apr. 26, 2006, eight pages.
U.S. Final Office Action dated Nov. 24, 2009, for U.S. Appl. No. 11/009,965, filed Dec. 10, 2004, fourteen pages.
U.S. Non Final Office Action dated Dec. 31, 2015 for U.S. Appl. No. 14/278,833, filed May 15, 2014, seven pages.
U.S. Non-Final Office Action dated Jan. 12, 2018, for U.S. Appl. No. 14/975,707, filed Dec. 18, 2015, seven pages.
U.S. Non Final Office Action dated Jan. 29, 2014 for U.S. Appl. No. 13/585,824, filed Aug. 14, 2012, five pages.
U.S. Non Final Office Action dated Mar. 25, 2015 for U.S. Appl. No. 13/585,824, filed Aug. 14, 2012, ten pages.
U.S. Non Final Office Action dated Oct. 23, 2015 for U.S. Appl. No. 14/140,370, filed Dec. 24, 2013, eight pages.
U.S. Non Final Office Action dated Dec. 22, 2016, for U.S. Appl. No. 13/585,824, filed Aug. 14, 2012, eight pages.
U.S. Non-Final Office Action dated Apr. 2, 2009, for U.S. Appl. No. 11/009,965, filed Dec. 10, 2004, thirteen pages.
U.S. Non-Final Office Action dated Aug. 16, 2013, for U.S. Appl. No. 12/761,462, filed Apr. 16, 2010, ten pages.
U.S. Non-Final Office Action dated Aug. 16, 2013, for U.S. Appl. No. 12/761,523, filed Apr. 16, 2010, nine pages.
U.S. Non-Final Office Action dated Dec. 10, 2010, for U.S. Appl. No. 11/412,715, filed Apr. 26, 2006, ten pages.
U.S. Non-Final Office Action dated Dec. 14, 2011, for U.S. Appl. No. 11/412,715, filed Apr. 26, 2006, eight pages.
U.S. Non-Final Office Action dated Jan. 2, 2008, for U.S. Appl. No. 11/122,267, filed May 4, 2005, five pages.
U.S. Non-Final Office Action dated Jan. 20, 2016, for U.S. Appl. No. 14/629,473, filed Feb. 23, 2015, fourteen pages.
U.S. Non-Final Office Action dated Jul. 17, 2003, for U.S. Appl. No. 09/905,642, filed Jul. 13, 2001, six pages.
U.S. Non-Final Office Action dated Jul. 5, 2016, for U.S. Appl. No. 14/975,707, filed Dec. 18, 2015, four pages.
U.S. Non-Final Office Action dated Jun. 1, 2007, for U.S. Appl. No. 10/899,648, filed Jul. 26, 2004, seven pages.
U.S. Non-Final Office Action dated Jun. 14, 2011, for U.S. Appl. No. 12/278,740, filed Dec. 10, 2008; 15 pages.
U.S. Non-Final Office Action dated Jun. 20, 2008, for U.S. Appl. No. 11/009,398, filed Dec. 10, 2004, fifteen pages.
U.S. Non-Final Office Action dated Jun. 23, 2010, for U.S. Appl. No. 11/009,965, filed Dec. 10, 2004, fourteen pages.
U.S. Non-Final Office Action dated Jun. 9, 2011, for U.S. Appl. No. 11/830,323, filed Jul. 30, 2007, five pages.
U.S. Non-Final Office Action dated May 18, 2004, for U.S. Appl. No. 10/050,601, filed Jan. 15, 2002, eight pages.
U.S. Non-Final Office Action dated Nov. 23, 2009, for U.S. Appl. No. 11/969,974, filed Jan. 7, 2008, seven pages.
U.S. Non-Final Office Action dated Sep. 12, 2014, for U.S. Appl. No. 14/154,177, filed Jan. 13, 2014, four pages.
U.S. Non-Final Office Action dated Sep. 27, 2016, for U.S. Appl. No. 14/140,370, filed Dec. 24, 2013, nine pages.
U.S. Non-Final Office Action with Restriction Requirement dated Mar. 4, 2011, for U.S. Appl. No. 11/830,323, filed Jul. 30, 2007, nine pages.
U.S. Notice of Allowability dated Jan. 2, 2008, for U.S. Appl. No. 10/899,648, filed Jul. 26, 2004, three pages.
U.S. Notice of Allowance dated Jan. 9, 2018, for U.S. Appl. No. 14/629,473, filed Feb. 23, 2015, nine pages.
U.S. Notice of Allowance dated Apr. 7, 2004, for U.S. Appl. No. 09/905,642, filed Jul. 13, 2001, six pages.
U.S. Notice of Allowance dated Aug. 23, 2017, for U.S. Appl. No. 13/585,824, filed Aug. 14, 2012, five pages.
U.S. Notice of Allowance dated Aug. 26, 2004, for U.S. Appl. No. 10/050,601, filed Jan. 15, 2002, four pages.
U.S. Notice of Allowance dated Aug. 6, 2015, for U.S. Appl. No. 13/853,656, filed Mar. 29, 2013, seven pages.
U.S. Notice of Allowance dated Feb. 25, 2010, for U.S. Appl. No. 11/969,974, filed Jan. 7, 2008, four pages.
U.S. Notice of Allowance dated Jul. 28, 2017, for U.S. Appl. No. 14/629,473, filed Feb. 23, 2015, ten pages.
U.S. Notice of Allowance dated Mar. 28, 2016, for U.S. Appl. No. 13/853,656, filed Mar. 29, 2013, eight pages.

(56) References Cited

OTHER PUBLICATIONS

U.S. Notice of Allowance dated Nov. 23, 2015, for U.S. Appl. No. 13/853,656, filed Mar. 29, 2013, seven pages.
U.S. Notice of Allowance dated Oct. 10, 2014, for U.S. Appl. No. 12/761,462, filed Apr. 16, 2010, ten pages.
U.S. Notice of Allowance dated Oct. 5, 2007, for U.S. Appl. No. 10/899,648, filed Jul. 26, 2004, six pages.
U.S. Notice of Allowance dated Jan. 5, 2017, for U.S. Appl. No. 14/278,833, filed May 15, 2014, seven pages.
U.S. Notice of Allowance dated Sep. 10, 2013, for U.S. Appl. No. 11/412,715, filed Apr. 26, 2006, eight pages.
U.S. Notice of Allowance dated Sep. 14, 2012, for U.S. Appl. No. 11/830,323, filed Jul. 30, 2007, eight pages.
U.S. Notice of Allowance dated Sep. 15, 2017, for U.S. Appl. No. 13/585,824, filed Aug. 14, 2012, five pages.
U.S. Supplemental Notice of Allowability dated Mar. 10, 2005, for U.S. Appl. No. 10/050,601, filed Jan. 15, 2002, five pages.
U.S. Appl. No. 15/844,206, filed Dec. 15, 2017.
Written Opinion of the International Searching Authority dated Aug. 3, 2006, for International Application No. PCT/CA2006/000669 filed Apr. 27, 2006, eight pages.
Written Opinion of the International Searching Authority dated Dec. 7, 2007, for International Application No. PCT/CA2007/001335, filed Jul. 30, 2007, four pages.
Chinese Notice of Allowance dated Aug. 3, 2018, for Chinese Application No. 201480027537.5, filed on May 15, 2014, six pages.
Chinese Third Office Action dated Mar. 8, 2018 for Chinese Application No. 201480027537.5 filed May 15, 2014, thirteen pages.
European Office Action dated Jul. 27, 2018 for EP Application No. 14810752.7 filed on Sep. 8, 2016, three pages.
U.S. Non Final Office Action dated Jun. 19, 2018 for U.S. Appl. No. 15/844,206, filed Dec. 15, 2017, six pages.
U.S. Notice of Allowance dated Sep. 12, 2018, for U.S. Appl. No. 14/975,707, filed Dec. 18, 2015, eight pages.
U.S. Appl. No. 15/948,890, filed Apr. 9, 2018. (Copy not submitted herewith pursuant to the waiver of 37 C.F.R. § 1.98(a)(2)(iii) issued by the Office on Sep. 21, 2004.).

\* cited by examiner

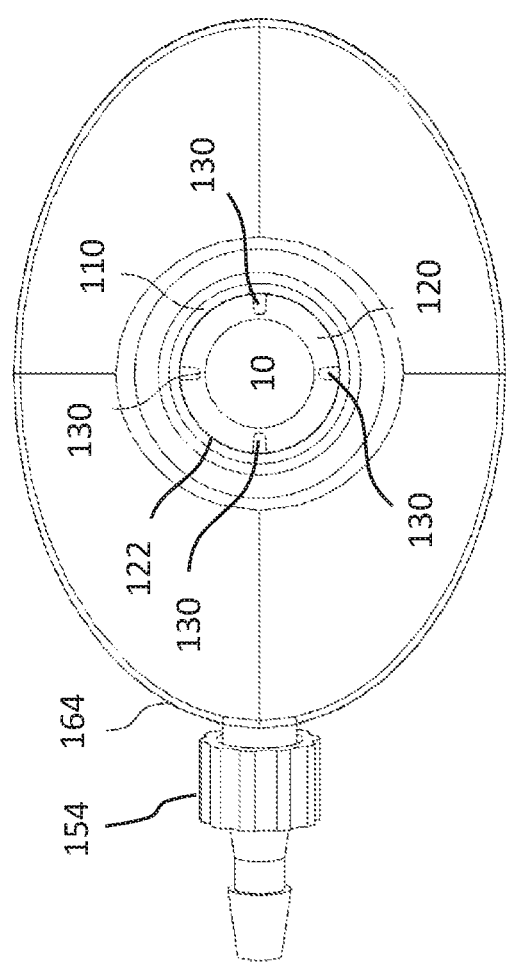

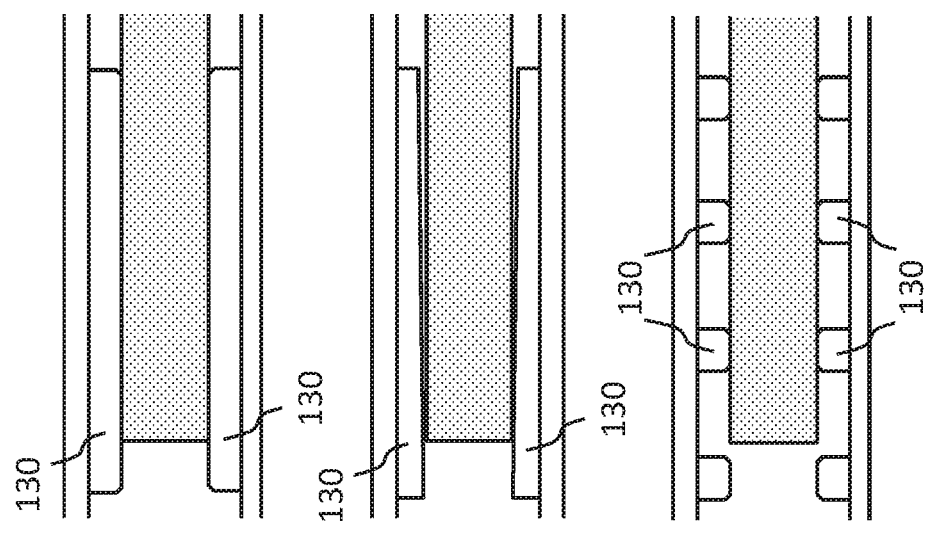

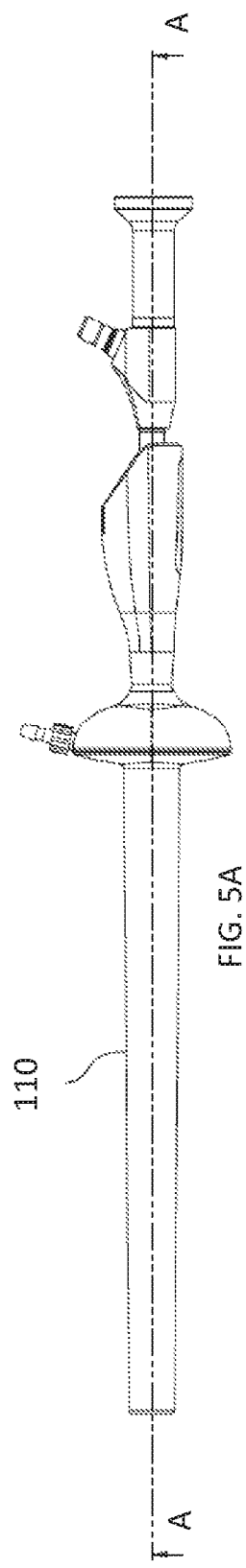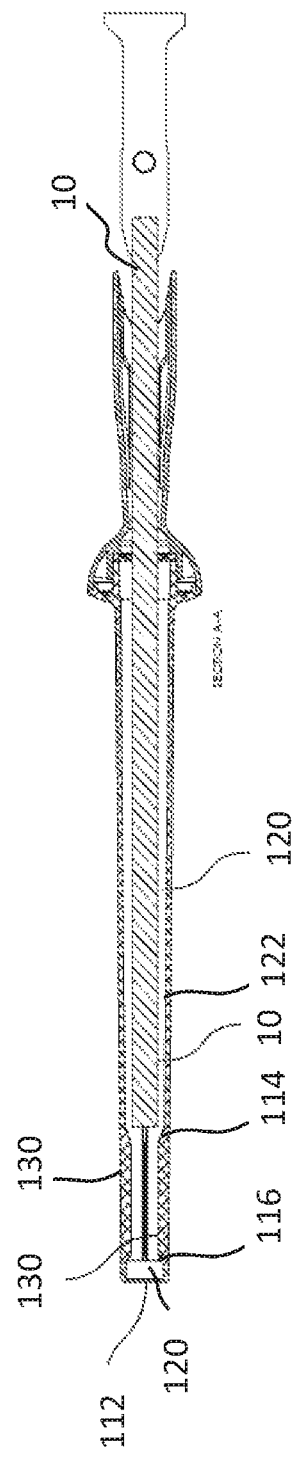
FIG. 5A
FIG. 5B

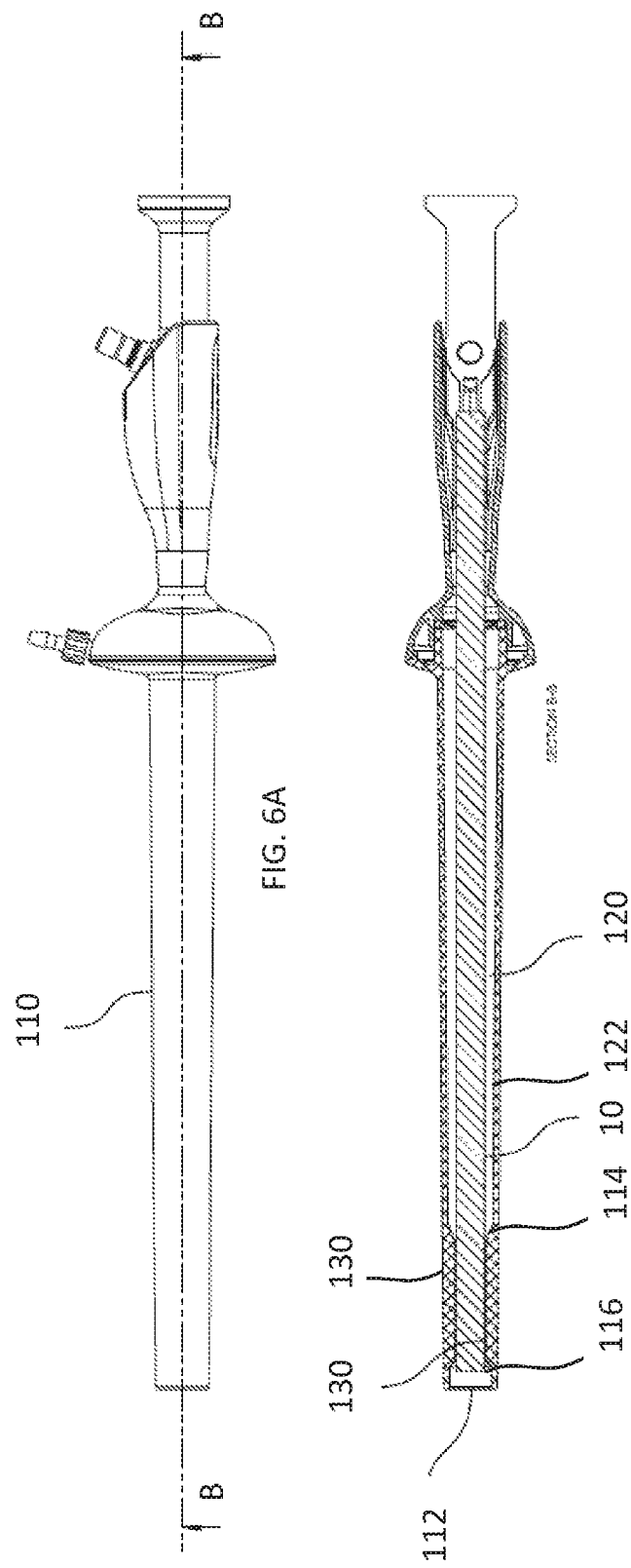

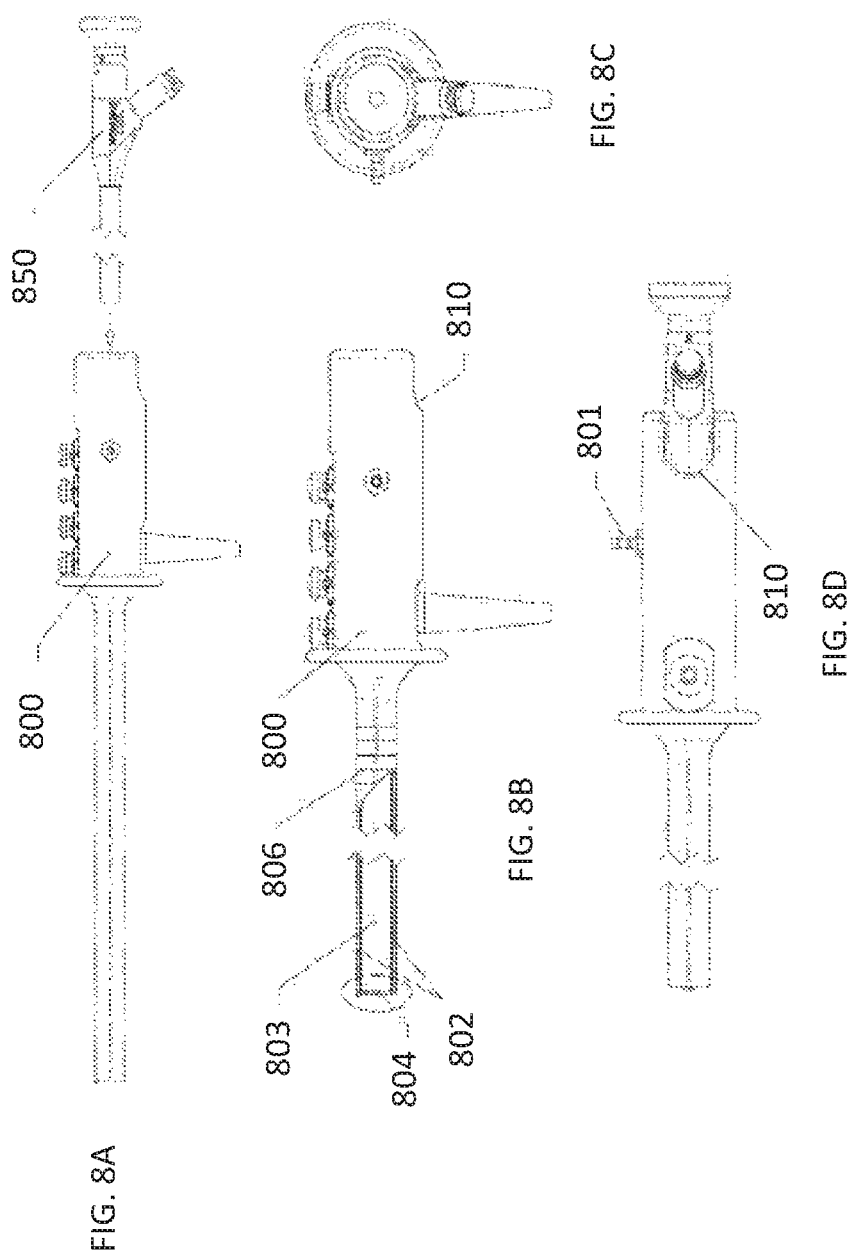

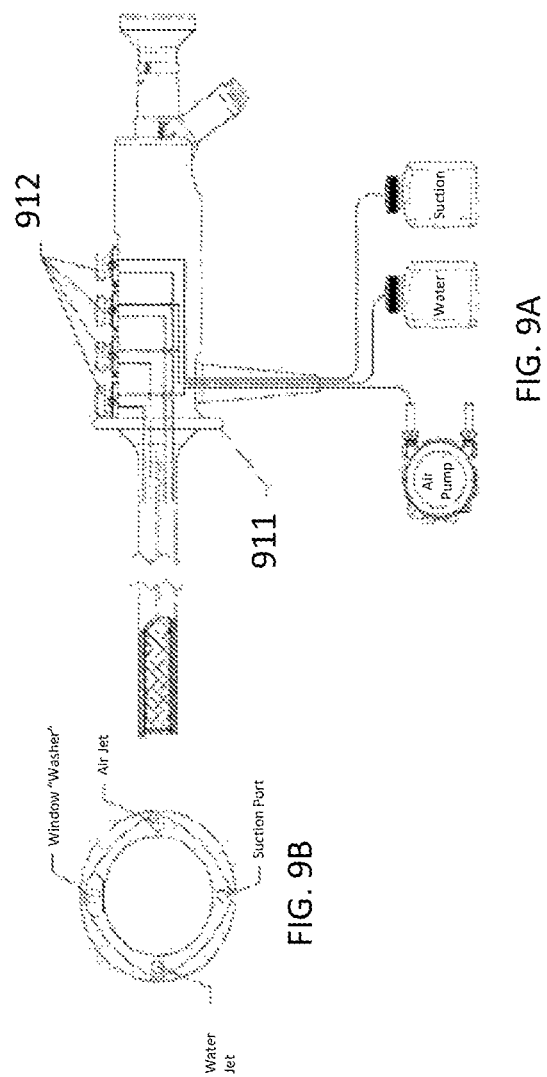

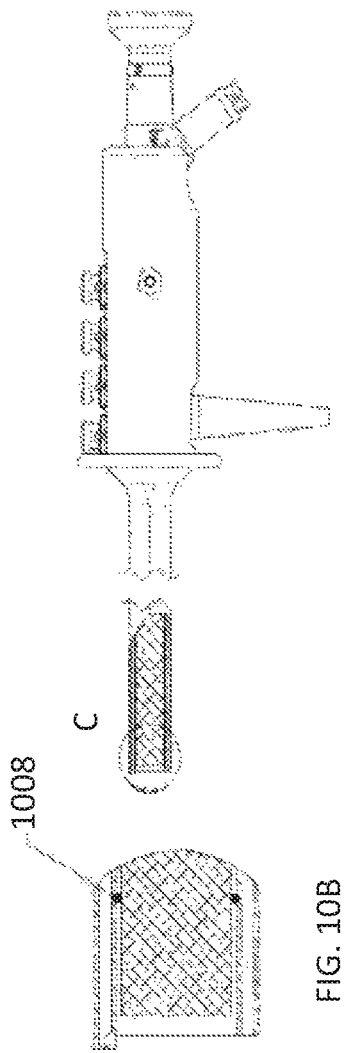

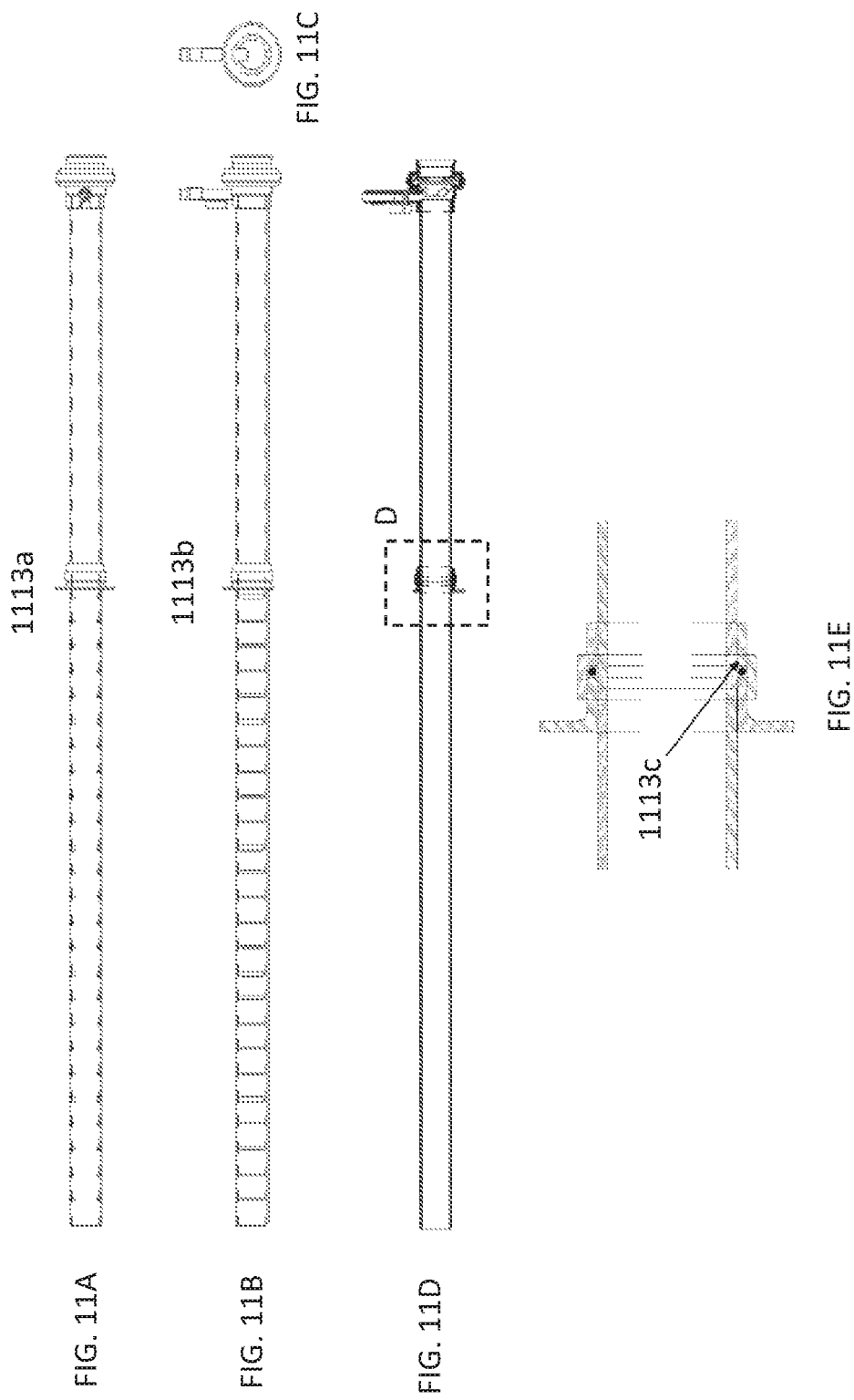

ENDOLUMINAL INTRODUCER WITH CONTAMINATION AVOIDANCE

BACKGROUND OF THE INVENTION

Low anterior resection (LAR) is a common surgical treatment for rectal cancer in which the cancerous segment of the rectum is removed and remaining segments of the rectum are reconnected. This procedure is commonly performed using minimally-invasive surgical techniques. Upon completion of an LAR surgery, the surgeon may want to perform a post-operative trans-anal examination of the suture line within the rectum, or the anastomosis. One purpose of the endoluminal examination is to confirm that the tissue surrounding the anastomosis is well perfused with blood, as such perfusion indicates that the healing process will be successful and that leaks (e.g., leaks of fecal matter into the peritoneum and resulting complications) are less likely to occur. Failure of the anastomosis, often taking the form of anastomotic dehiscence, is a devastating complication of LAR surgery. In the short term, sepsis resulting from fecal leaks can result in acute effects, and even death. Long term morbidities associated with anastomotic failure include stricture formation, bowel dysfunction and an increased chance of cancer recurrence. Ischemia of the tissue surrounding the anastomosis is the likely cause of the majority of complications. Accordingly, accurate post-operative examination of the anastomosis may be crucial to avoid these complications.

The post-operative endoluminal examination is commonly performed with the use of a conventional endoscopic imaging device such as a sigmoidoscope, proctoscope, rectoscope, or colonoscope, etc. There are modern fluorescence-capable laparoscopes that offer several advantages over these conventional instruments, such as higher camera resolution (e.g., high-definition image capability) and the added functionality of tissue perfusion assessment. However, these laparoscopes do not include many practical features that are useful for endoluminal examination. Most notably, these laparoscopes lack the ability to insufflate the rectum, as well as the ability to wash and aspirate fluids from the endoluminal surface to facilitate proper imaging of the anastomosis. To solve this problem, such modern laparoscopes may be used in combination with a surrounding introducer device providing these additional capabilities.

Existing laparoscope introducers typically suffer from the inability to adequately prevent the laparoscope lens from becoming obscured by debris during the insertion of the laparoscope/introducer combination into the rectum, and during the examination procedure itself. Such contamination or occlusion may interfere with visibility during the examination and make it difficult to perform a thorough and accurate assessment of the tissue in the body cavity. As a result, the endoluminal instrument must be removed, cleaned, and reinserted at intervals during the procedure, which complicates the examination procedure and wastes time.

Thus, an endoluminal introducer device and method for using an endoluminal introducer device that reduce the likelihood of debris contaminating and obscuring the laparoscope lens during an examination procedure of a body cavity are desirable.

BRIEF SUMMARY OF THE INVENTION

Described herein are variations of introducer devices for an endoluminal instrument. Generally, in some variations, an introducer device may include a tubular member having an inner wall that defines a channel configured to receive at least a portion of the endoluminal instrument, and a plurality of projections disposed in the channel at perimetrically spaced apart locations around the inner wall. The projections may extend inward and be configured to offset the endoluminal instrument from the inner wall, thereby creating a space between the endoluminal instrument and the inner wall. In some variations, the introducer device may include a port such as an insufflation port coupled to the tubular member and configured to pass insufflation gas into the channel.

In some variations, the projections may be disposed in a distal segment of the channel. In some variations, a distal end of the channel may be in fluid communication with the space between the endoluminal instrument and the inner wall. In some variations, the projections may be approximately radially symmetrically arranged around the inner wall. In some variations, the projections may be integrally formed with the inner wall.

In some variations, at least one projection may include a longitudinal ridge extending along the channel. In some variations, the longitudinal ridge may be of approximately uniform height along its longitudinal axis, while in some variations at least a portion of the longitudinal ridge may be sloped along its longitudinal axis. In some variations, a distal endpoint of the longitudinal ridge may be located proximal to the distal end of the tubular member. In some variations, the projections may include at least four longitudinal ridges equally distributed around the inner wall. In some variations, at least one projection may include an approximately round bump.

In some variations, the tubular member may define a first instrument insertion depth reference that indicates a first position for the endoluminal instrument relative to the tubular member, and a second instrument insertion depth reference that indicates a second position for the endoluminal instrument relative to the tubular member. In some variations, at least one of the first and second instrument insertion depth references includes tactile feedback resulting from interference between at least one of the projections and the endoluminal instrument. In some variations, at least one of the first and second instrument insertion depth references includes a visual reference on the tubular member. In some variations, the visual reference may include a reference line.

Also described herein are variations of methods for using an introducer device to facilitate passing an endoluminal instrument to a target region of a body cavity. Generally, in some variations, the method may include passing the endoluminal instrument within the introducer device to a first instrument insertion depth, advancing the introducer device toward the target region of the body cavity, and advancing the endoluminal instrument within the introducer device to a second instrument insertion depth that is distal to the first instrument insertion depth. When the endoluminal introducer is at the second instrument insertion depth, there may be a space between the endoluminal instrument and an inner wall of the introducer device.

In some variations, advancing the endoluminal instrument includes centering the endoluminal instrument within the introducer device. In some variations, passing the endoluminal instrument within the introducer device to a first instrument insertion depth includes positioning the endoluminal instrument at least partially based on tactile feedback resulting from interference between the endoluminal instrument and an internal projection of the introducer device. In some variations, passing the endoluminal instrument within the introducer device to a first instrument insertion depth includes positioning the endoluminal instrument at least partially based on a visual reference on the introducer device. In some variations, advancing the endoluminal instrument within the introducer device to a second instrument insertion depth includes positioning the endoluminal instrument at least partially based on a visual reference on the introducer device.

BRIEF DESCRIPTION OF THE DRAWINGS

FIG. 3 is a distal view of an illustrative embodiment of an introducer device receiving an endoscope.

FIGS. 4A-4C are schematic depictions of variations of projections in illustrative embodiments of an introducer device.

FIG. 5A is a side view of an illustrative embodiment of an introducer device receiving an endoscope during a first stage of instrument insertion. FIG. 5B is a cutaway view along the line A:A in FIG. 5A.

FIG. 6A is a side view of an illustrative embodiment of an introducer device receiving an endoscope during a second stage of instrument insertion. FIG. 6B is a cutaway view along the line B:B in FIG. 6A.

FIGS. 8A-8D depict another variation of an introducer device.

FIGS. 9A and 9B depict another variation of an introducer device.

FIGS. 10A and 10B depict another variation of an introducer device.

FIGS. 11A-11E depict connection mechanisms in variations of an introducer device.

DETAILED DESCRIPTION OF THE INVENTION

Figure 1:
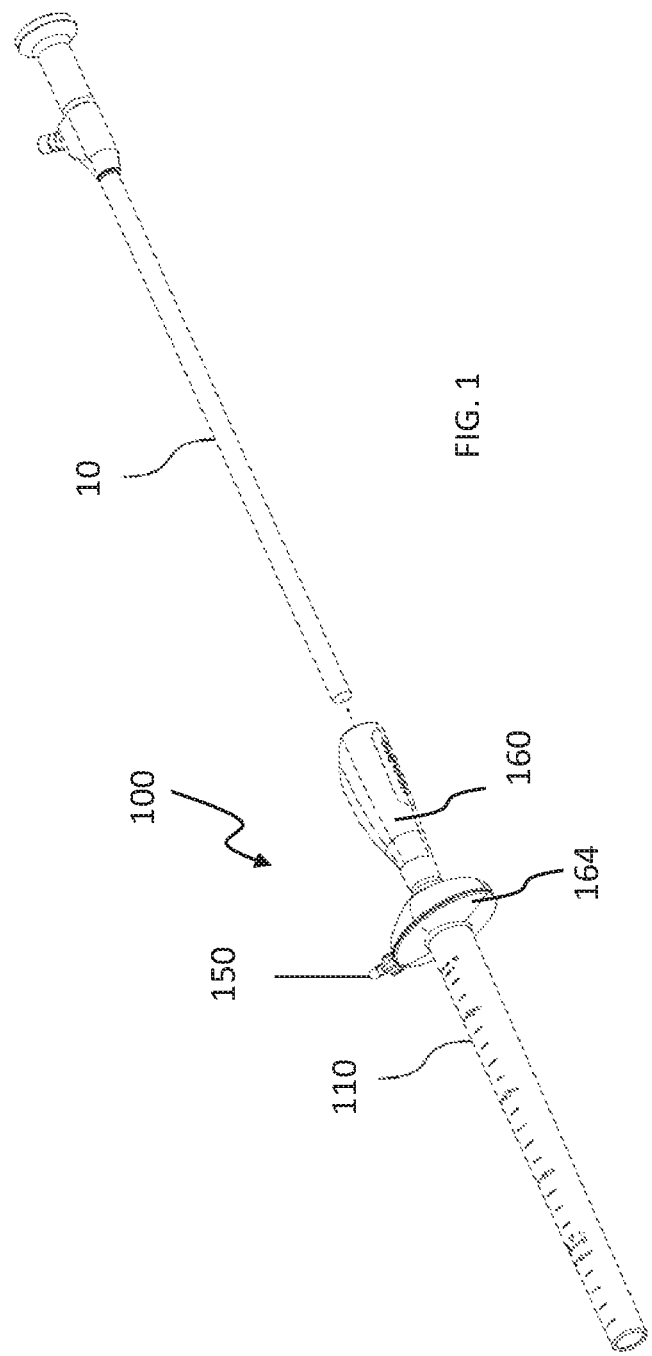
FIG. 1 is an illustrative depiction of an embodiment of an introducer device in relation to an endoscope.

Described herein are variations of an introducer device and methods for using an introducer device to pass an endoluminal instrument to a target region of a body cavity. For example, the introducer device may be used in conjunction with a laparoscope for endoluminal examination following LAR surgery. In this example, the introducer may act as a conduit for introducing the laparoscope into a subject's rectum and enables the viewing of the endoluminal surface and surgical margin or anastomosis formed in the LAR surgical procedure. In other examples, the introducer may act as a conduit for the laparoscope or another suitable endoluminal instrument for enabling viewing of other body cavities (e.g., esophagus). The introducer may incorporate features useful for examination of the endoluminal surface with the laparoscope and/or features that reduce the likelihood of contamination, as described herein.

In some variations, the endoluminal introducer may be used in conjunction with a laparoscope that is capable of near infrared illumination and imaging, such that the anastomosis may be viewed using an ICG imaging agent to highlight the perfusion of tissue at and around the area of the surgery. One example of such a laparoscope is the PIN-POINT® system (Novadaq Technologies Inc., Canada) that provides for simultaneous white light and near infrared illumination and imaging. This allows for enhanced visualization and assessment of the anastomosis and surgical margin over that which can be achieved with conventional white light endoscopes. In other variations, the endoluminal introducer may be used in conjunction with any other suitable endoscope or endoluminal instrument.

Introducer Device

In some variations, the introducer device for an endoluminal instrument includes a tubular member having an inner wall that defines a channel configured to receive at least a portion of the endoluminal instrument, and a plurality of projections disposed in the channel at perimetrically spaced apart locations around the inner wall of the tubular member. The projections may extend inward and be configured to offset the endoluminal instrument from the inner wall, thereby creating a space between the endoluminal instrument and the inner wall.

In some variations, the space between the endoluminal instrument and the inner wall enable passage of debris, fluids, or a combination thereof that may enter the introducer device, such as during insertion and advancement of the introducer device and endoluminal instrument into the body cavity. In particular, any entering debris and/or fluids may flow into the space between the endoluminal instrument and the inner wall instead of occluding or otherwise contaminating the distal end of the endoluminal instrument (e.g., lens of an endoscope) and other portions of the endoluminal instrument. Additionally or alternatively, in some variations the introducer device may include features that indicate to the user one or more recommended relative longitudinal positions of the endoluminal instrument and introducer device (i.e., instrument insertion depths) during a method for using an introducer device to facilitate passing the endoluminal instrument into and through a body cavity. The recommended instrument insertion depths may help reduce the likelihood of contamination of the distal end of the endoluminal instrument when the endoluminal instrument is inserted, advanced, and/or otherwise repositioned within the body cavity. Avoiding the need for removal and repositioning of the endoluminal instrument may save time and hassle, as well as avoid fogging of lenses and other hardware potentially resulting from the removal and reintroduction of an endoluminal device.

As shown in FIG. 1, the introducer device 100 comprises a tubular member 110 that is configured to receive at least a distal portion of an endoluminal instrument 10 (e.g., endoscope). As pictured, the distal end of the endoluminal instrument 10 may be inserted into a proximal end of the introducer device 100. However, the introducer device 100 may receive the endoluminal instrument 10 in any suitable fashion.

Figure 2:
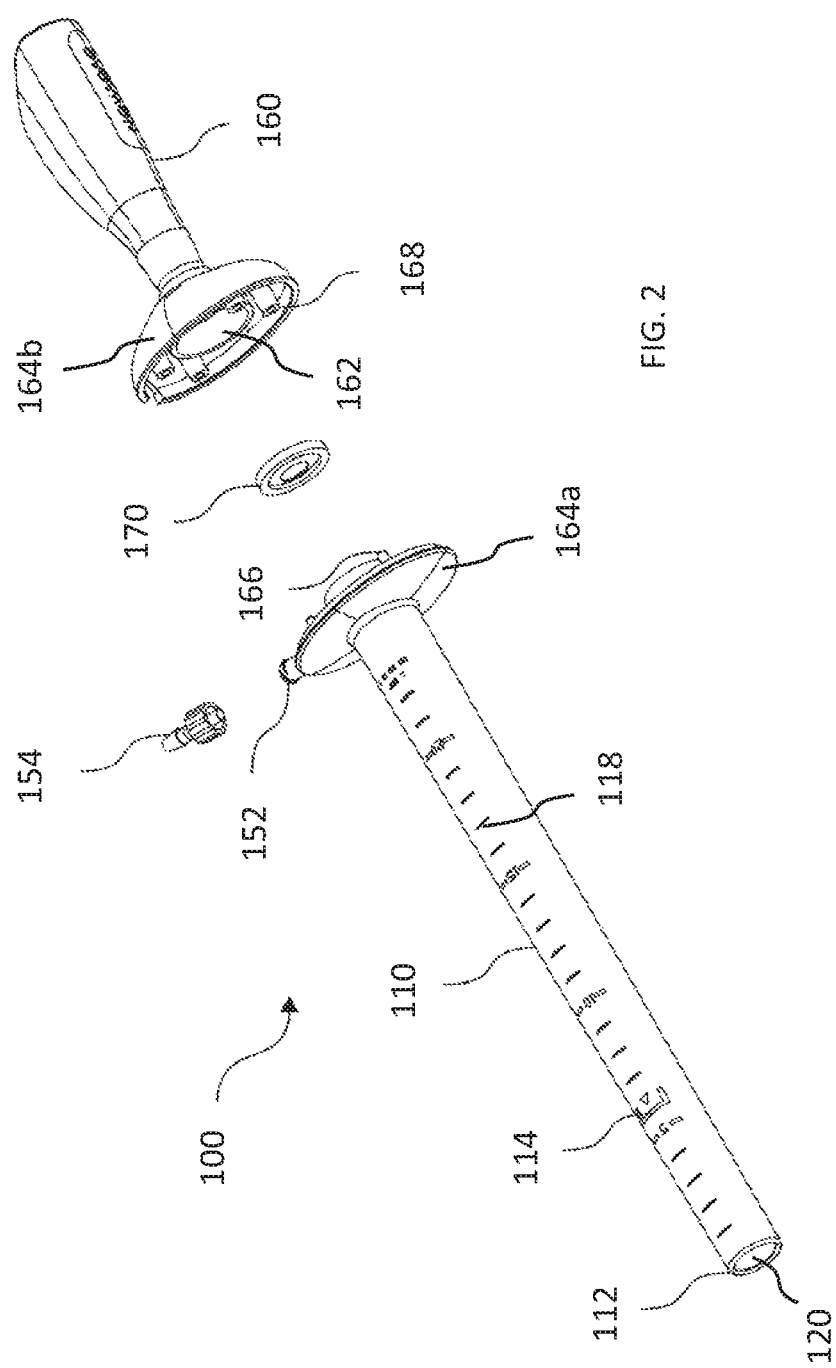
FIG. 2 is an exploded view of an illustrative embodiment of an introducer device.

As shown in more detail in FIG. 2, in some variations, at least a portion of the tubular member 110 may be conical or frustoconical, tapering at its distal end 112. Such a shape may, for example, help to dilate the body cavity as the introducer device 100 is inserted into and distally advanced within the body cavity. The distal end 112 may be rounded so as to reduce the chance of injury to tissue when the introducer device 100 is inserted and advanced in a body cavity. The distal end 112 may have other atraumatic features, such as including a softer, relatively flexible or compliant material (e.g., rubber). In other variations, the tubular member 110 may have generally the same or constant outer diameter along its length. In some variations, the distal end of the tubular member has an outer diameter measuring between about 1 cm and about 2 cm. In some variations, the tubular member has a length between about 20 cm and about 30 cm. For instance, in an exemplary embodiment the tubular member is at least about 25 cm and may be inserted into a body cavity to a depth of up to about 25.5 cm, which may enable the endoluminal instrument to gain access to a greater variety of target areas within the body cavity. However, the tubular member may have any suitable dimensions. The dimensions may depend, for example, on the particular application (e.g., general type, diameter, and shape of body cavity, distance to target region in the body cavity, and/or size of endoluminal instrument).

As shown in FIG. 2, the tubular member 110 may include a reference (e.g., one or more reference lines 118) to indicate depth of insertion of the introducer device into a body cavity. Some or all of the references lines may be numerically numbered to represent particular depth increments (e.g., 0.5 cm, 1 cm, etc.). In some variations, one or more of the reference lines 118 may include decals (e.g., printed or inked) applied onto an internal and/or external surface of the tubular member. In some variations, one or more of the references lines 118 may be formed by altering the material of the tubular member itself, such as by etching or altering the material finish and/or color at desired increments along the length of the tubular member. In some variations, one or more of the insertion depths may be indicated by a change in the cross-section or other geometry of the tubular member 110 at that particular location. For example, one or more of the insertion depths may be indicated by a change in outer diameter (e.g., a ridge or groove).

As shown in FIG. 3, the tubular member 110 may have an inner wall 122 that defines a channel 120 that is configured to receive an endoluminal instrument 10. The channel may have a generally circular cross-section, though in other variations the channel may have an oval, square, irregular, or any other suitable cross-section. In some variations, the channel 120 is of a generally constant diameter along the length, though in other variations the channel 120 may taper toward its distal end or otherwise vary in diameter along its length. In variations in which the tubular member has a length between about 20 cm and about 30 cm, the channel may, for example, have a diameter between about 0 cm and about 1 cm, or between about 0.25 cm and about 0.75 cm. In other variations, the channel may have other dimensions that may depend on, for example, the particular size and shape of endoluminal instrument with which the introducer device is to be used.

As shown in FIG. 3, a plurality of projections 130 may be disposed in the channel 120 of the tubular member. The projections may be located in a distal segment of the channel 120. The projections 130 may extend inward from the inner wall 122 of the tubular member into the channel 120, such that when the endoluminal instrument 10 is received in the segment of the channel where the projections are located, the projections radially offset the endoluminal instrument 10 away from the inner wall. This offset of the endoluminal instrument 10 from the inner wall 122 may result in a space between the endoluminal instrument and the inner wall. As best shown in FIGS. 5B and 6B, in segments of the channel 120 that lack the projections 130, the space may include an annular space between the endoluminal instrument 10 and the inner wall 122.

The space between the endoluminal instrument 10 and the inner wall 122 of the tubular member may be in fluidic communication with a distal end 112 of the channel such that any debris and/or fluids that happen to enter the distal end 112 of the channel (e.g., during insertion or repositioning of the introducer device in the body cavity, during examination) is able to flow around and proximally past the distal end of the endoluminal instrument, thereby reducing or preventing accumulation of debris at the distal end of the endoluminal instrument. For instance, in cases in which the endoluminal instrument is a laparoscope with a lens at its distal end, the space between the laparoscope and the inner wall 122 helps prevent accumulation of debris and other contamination from occluding the lens.

The projections 130 may be perimetrically arranged around the inner wall 122 of the tubular member to offset the endoluminal instrument from the inner wall 122. For example, in an embodiment in which the channel has a circular cross-section, the projections may be arranged circumferentially around the channel on the inner wall. In some variations, some or all of the projections may be arranged in a ring-like manner, such that a subset or all of the projections are located at approximately the same longitudinal location within the channel 120. In some variations, some or all of the projections 130 may have different longitudinal locations (e.g., arranged in a helical manner) within the channel 120. The particular arrangement of the projections 130 (e.g., number, size, shape, spacing) within the channel 120 may generally be selected so as to permit fluidic communication along the channel 120 between the projections 130 and within the space between the endoluminal instrument 10 and the inner wall 122.

In some variations, the projections 130 are configured to generally center the endoluminal instrument 10 along the longitudinal axis of channel 120. For instance, the projections 130 may be generally radially symmetrical about the channel 120, or at least the projections 130 may have about equal heights (i.e., project about the same distance inward), in order to radially offset the endoluminal instrument 10 from the inner wall 122 by generally the same amount. However, in other variations at least some of the projections 130 may have different heights such that the endoluminal instrument 10 is not generally centered along the longitudinal axis of the channel 120, while the projections 130 still maintain for some space or other clearance between the endoluminal instrument 10 and at least one side of the inner wall 122 of the tubular member 110. Additionally, the projections may be equally or unequally distributed around the inner wall 122 of the tubular member 110.

The projections 130 may have any suitable shape (e.g., in terms of profile, length, etc.) to offset the endoluminal instrument 10 from the inner wall 122. In some variations, the surface of the projections that contact the endoluminal instrument 10 may conform to the endoluminal instrument surface, such as by having a concave surface corresponding to the radius of curvature of the endoluminal instrument surface, and/or including a conformable material such as rubber. In some variations, some or all of the projections 130 may include a longitudinal ridge extending along the channel. For example, the longitudinal ridge may be of approximately uniform height along its longitudinal axis (FIG. 4A) or the longitudinal ridge may be sloped along its longitudinal axis (FIG. 4B), similar to a ramp. In some variations, some or all of the projections 130 may include bumps (e.g., a round or circular bump such as that as shown in FIG. 4C), detents, partial rings, or other suitable shapes that project inward into the channel 120. In some variations, the edges of the projections 130 may be rounded so as to reduce the likelihood of damage to the endoluminal instrument 10. In some variations, the distalmost endpoint or surface of the projections may be located proximal to the distal end of the tubular member, leaving the distal end of the channel unobstructed.

In some variations, one or more of the projections are integrally formed (e.g., by injection molding) with the inner wall 122 of the tubular member 110 while in some variations, one or more of the projections are formed separately and coupled to the inner wall 122 such as with epoxy. The projections may be made of the same material as the tubular member (e.g., a rigid plastic, as described further below) and/or other materials such as silicone, or other rubber or elastomer.

In some variations, as shown in FIG. 2, the tubular member may define one or more instrument insertion depth references that indicate the position of an inserted endoluminal instrument relative to the introducer device 100. As described further below, one or more of the instrument insertion depth references may also provide recommended instrument insertion depths in an insertion method for using an introducer device that reduces contamination risk when positioning the introducer device in a target region of a body cavity.

In some variations, the tubular member may define a first instrument insertion depth reference 114 that indicates a first position for the endoluminal instrument relative to the tubular member 110. This first position may, in some variations, be a suitable recommended first instrument insertion depth in the insertion method described below. In some variations, the first instrument insertion depth reference 114 may include tactile feedback. For example, as illustrated in FIG. 5B, the tactile feedback may result from interference between at least one of the projections 130 and the endoluminal instrument 10. In particular, a user of the device who is advancing the endoluminal instrument 10 within the channel 120 may feel resistance when the endoluminal instrument 10 encounters and physically interferes with one or more of the projections 130 present within channel 120. As another example, the tactile feedback may result from a removable physical stop (e.g., an inflatable or slidable stop that is temporarily located at the first instrument insertion depth. In particular, similar to the preceding example, a user of the device may feel resistance when the endoluminal instrument 10 encounters and physically interferes with the removable physical stop.

In some variations, the first instrument insertion depth reference 114 includes a visual reference on the tubular member. For example, as illustrated in FIG. 2, the visual reference for first instrument insertion depth reference 114 may be similar to a depth reference 118 described above, in that the first instrument insertion depth reference 114 may be a decal, etch, difference in material or color or finish, etc.

In some variations, as shown in FIGS. 5B and 6B, the tubular member may define a second instrument insertion depth reference 116 that indicates a second position for the endoluminal instrument 10 relative to the tubular member 110. This second position may, in some variations, be a suitable recommended second instrument depth in the insertion method described below. In some variations, the second instrument insertion depth reference 116 may be located proximal to the distal end 112 of the tubular member 110, set back from the distal end 112 by a distance that does not obstruct the angle or field of view of a lens on the endoluminal instrument. For instance, in variations in which the tubular member has a length between about 20 cm and about 30 cm, the second instrument insertion depth reference 116 may be located about 1 cm to about 2 cm proximal to the distal end of the tubular member 110. In these variations, the tubular member 110 may protrude distally beyond the end of the endoluminal instrument 10 when the endoluminal instrument 10 is positioned at the recommended second instrument depth reference 116, such that the additional length of the tubular member 110 may provide some protection for the endoluminal instrument 10. The second instrument insertion depth reference 116 may include tactile feedback and/or visual reference, similar to the first instrument insertion depth reference 114.

In one exemplary embodiment, the introducer device 100 may include four longitudinal ridges 130 that are equally distributed around the inner wall 122 and projecting into the channel 120, as shown in FIG. 3. As shown in FIGS. 5B and 6B, in variations in which the tubular member has a length between about 20 cm and about 30 cm, each of the longitudinal ridges is about 4-5 cm long and may longitudinally extend between a proximal point located about at the first instrument insertion depth at reference feature 114 and a distal point located proximal to the distal end 112 of the tubular member (e.g., about 1-2 cm proximal to the distal end 112). In some embodiments, each of the longitudinal ridges may extend until a distal point located proximal to the second instrument insertion depth reference 116.

As shown in FIG. 1, in some variations, the introducer device 100 may include an insufflation port 150 configured to receive and pass insufflation gas (e.g., air, carbon dioxide, etc.) into the channel 120 of the tubular member 110. The insufflation port 150 may include, for example, threaded connector 152 that couples to luer barb 154 as shown in FIG. 2, where luer barb 154 in turn is configured to couple to tubing and/or an insufflation gas source such as an insufflation bulb or pump (not shown). Other variations of the insufflation port 150 may include any suitable connection mechanisms, such as a hose barb, etc. The insufflation port 150 may be in fluid communication with the channel 120 such that insufflation gas may be introduced into the body cavity to increase visibility and access of the body cavity (e.g., to enable clearer assessment during a post-LAR examination).

In some variations, the introducer device 100 may include one or more ports to enable the introduction of irrigation or washing fluids (e.g., saline) or other agents (e.g., solid, fluid, or gas pharmaceutical compositions or agents, etc.) to the channel 120 or other channels in the introducer device 100. In some variations, the introducer device 100 may include one or more ports through which suction can be applied by a vacuum pump, such as to provide aspiration capabilities. Such irrigation and suction capabilities may help remove any contamination that does accumulate on or near the endoluminal instrument and reduce the need to remove the endoluminal instrument from the introducer device for cleaning. The port for irrigation fluid and/or the port for suction may be the same as the insufflation port 150, or may be located in the introducer device separate from the insufflation port 150.

In some variations, as shown in FIGS. 1 and 2, the introducer device 100 may include a handle 160. The handle 160 may be coupled to the proximal end of the tubular member 110. The handle 160 may be removable from the tubular member, or may be substantially permanently joined to the tubular member. The handle 160 may include a handle channel 162 that is axially aligned with the channel 120 of the tubular member 110 and configured to receive the endoluminal instrument 10. The handle 160 may include ergonomic features to better facilitate maneuvering of the introducer device 100. For example, the handle may include a curved or bulbous-like grip for the user to comfortably hold, concavities or grooves for placement of the user's fingers, and/or frictional features such as ribbing or elastomeric material to increase the ability of the user to grip the handle. In some variations, the handle may include a proximal flare or flange, similar to the flange 164 below, against which the hand of the user may brace when removing the introducer device 100 or repositioning the introducer device 100 in the body cavity.

In some variations, the handle 160 may couple to the endoluminal instrument 10 when the endoluminal instrument 10 is received in the handle channel 162. For instance, the handle 160 may include a snap fit or friction fit feature, or other suitable mechanism, that temporarily locks the axial position and/or rotational position of the endoluminal instrument 10 relative to the introducer device 100, such that the endoluminal instrument 10 and the introducer device 100 may move together in tandem in at least longitudinal motion and/or rotational motion.

As shown in FIG. 1, the introducer device 100 may include a flange 164 that facilitates more ergonomic handling of the introducer device. For instance, a hand of the user may brace against the flange 164 when inserting and advancing the introducer device 100 into a body cavity. Although the flange 164 as shown in FIG. 1 is proximal to the handle 160, in other variations the flange 164 may be part of handle 160 or in any suitable location for assisting handling of the introducer device. As shown in FIG. 2, the flange may include a proximal component 164a coupled to the tubular member 110 and a distal component 164b coupled to the handle 160. However, in other variations the flange may be a separate component that couples to the tubular member and/or handle in any suitable manner (e.g., as a ring that slides over and then couples to the handle).

In some variations, as shown in FIG. 2, the introducer device 100 may include a sealing member 170 that provides a circumferential seal around the endoluminal instrument (not shown) when the endoluminal instrument is within the introducer device. The sealing member 170 may be arranged proximal to the insufflation port 150 to provide a proximal seal for substantially containing insufflation gas in the channel 120 of the tubular member and substantially preventing insufflation gas from exiting out the handle channel 162. For example, the sealing member 170 may include an O-ring or other gasket, ribbing, threaded features, or any other suitable sealing feature. The sealing member 170 may be a separate component or integrated with one or more other components of the introducer device.

The introducer device may be made at least partially of plastic (e.g., polypropylene, polycarbonate, polyethylene, polystyrene, K-resin, or other suitable rigid plastic, combinations thereof, etc.), and may be injection-molded to form the various features described above in the tubular member, channel, projections, handle, and other aspects of the introducer device. In some variations, the introducer device may be integrally formed through injection molding or other manufacturing processes. Various parts of the introducer device may be formed separately and coupled together in an assembly process. For instance, as shown in FIG. 2, the tubular member 110 and the handle 160 may be formed as separate components and coupled together by aligning and joining male pins 166 on the tubular member to the female pins 168 on the handle 160 (e.g., press-fit, with epoxy or fasteners, etc.). In other examples, the handle may be coupled to the tubular member via threads or mechanical interference (e.g., snap-fit).

Method of Use

Figure 7:
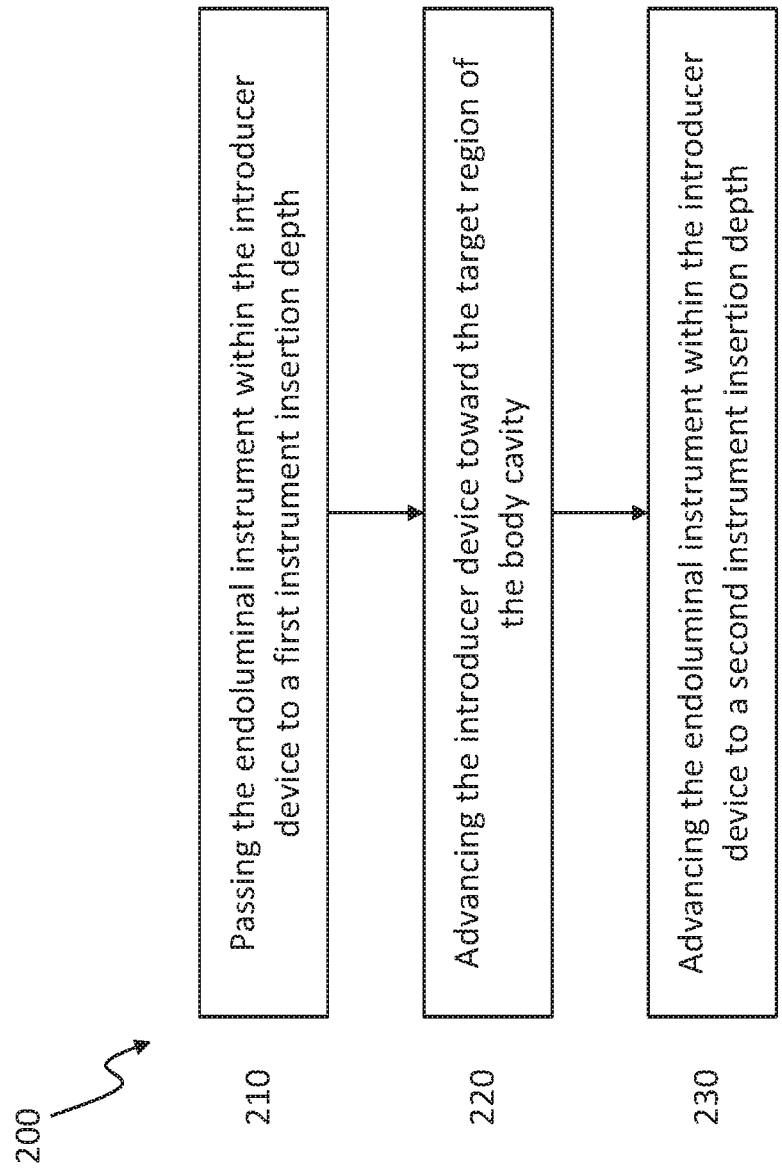
FIG. 7 is a schematic illustration of the method for using an introducer device to facilitate passing an endoluminal instrument to a target region of a body cavity.

In some variations, as shown in FIG. 7, a method 200 for using an introducer device to facilitate passing an endoluminal instrument to a target region of a body cavity includes: passing the endoluminal instrument within the introducer device to a first instrument insertion depth 210, advancing the introducer device toward the target region of the body cavity 220, and advancing the endoluminal instrument within the introducer device to a second instrument insertion depth 230, where the second instrument depth is distal to the first instrument insertion depth. When the endoluminal introducer is at the second instrument insertion depth, there may be a space between the endoluminal instrument and an inner wall of the introducer device.

The first and second instrument insertion depths may help reduce the likelihood of contamination of the distal end of the endoluminal instrument when the endoluminal instrument is at different stages of being inserted, advanced, and/or otherwise repositioned within the body cavity. Additionally or alternatively, as further described above with respect to the features of variations of an introducer device, any entering debris may flow into the space between the endoluminal instrument and the inner wall instead of occluding or otherwise contaminating the distal end of the endoluminal instrument (e.g., lens of an endoscope) and other portions of the endoluminal instrument.

In some variations, the method may include selecting the introducer device and/or endoluminal instrument such that the introducer device and endoluminal instrument are compatible in size and/or shape. For instance, the introducer device may be selected based on outer diameter, inner diameter at one or more points within a channel of the introducer device that receives the endoluminal instrument, length, material, shape (e.g., angles) of the introducer device, and/or the kind of functional features (e.g., irrigation, aspiration) in the introducer device. Additionally or alternatively, the endoluminal instrument may be selected in a similar fashion to be compatible with a particular introducer device.

In some variations, the method may include preparing the introducer device prior to passing the endoluminal instrument through the introducer device. For example, preparing the introducer device may include coupling an insufflation bulb (or pump, or other insufflation gas source) to the introducer device, sterilizing the endoluminal instrument, and/or lubricating the endoluminal instrument with a lubricant (e.g., petroleum jelly) to facilitate insertion of the introducer device into the body cavity.

Passing the endoluminal instrument within the introducer device to a first instrument insertion depth 200 positions the endoluminal instrument at a protective location within the introducer device where the distal end of the endoluminal instrument is recessed or set back from the distal end of the introducer device. An exemplary first instrument insertion depth is shown in FIGS. 5A and 5B, where the endoluminal instrument 10 is located at first instrument insertion depth reference 114. At this recessed, protective location, the endoluminal instrument (e.g., the lens of a laparoscope) is less likely to be contaminated by oncoming debris that may enter the distal end of the introducer device when the introducer device and endoluminal instrument combination is advanced through the body cavity. Additionally, at the first instrument insertion depth, the endoluminal instrument may still have an imaging field of view sufficient to provide a suitable amount of navigation visibility.

In some variations, the first instrument insertion depth may be between about 1 inch and about 6 inches from the distal end of the introducer device. In some variations, the first instrument insertion depth may be between about 2 inches and about 5 inches from the distal end of the introducer device. In some variations, the first instrument insertion depth may be between about 3 inches and about 4 inches from the distal end of the introducer device. However, the first instrument insertion depth may be any suitable distance that is sufficiently removed from the distal end of the introducer device while still enabling imaging visibility beyond the introducer device (e.g., for navigational purposes in the body cavity), or any other suitable depth.

In some variations, passing the endoluminal instrument within the introducer device to a first instrument insertion depth 200 may include positioning the endoluminal instrument at least partially based on tactile feedback. For example, the first instrument insertion depth may be indicated to the user as a result of interference between the endoluminal instrument and an internal projection of the introducer device. Such projections are described above with respect to variations of the introducer device. After inserting the distal end of the endoluminal instrument into the introducer device, the user may continue passing the endoluminal instrument through the introducer device at least until the user feels contact or resistance as a result of the endoluminal instrument encountering or abutting one or more internal projections. In some variations, the endoluminal instrument need not be passed farther after the initial contact or resistance. In other variations, the endoluminal instrument may continue to be passed slightly beyond the initial contact or resistance. In these variations, the internal projections may offset the endoluminal instrument away from an inner wall of the introducer device, thereby forming a space between the endoluminal instrument and the inner wall of the introducer device through which debris may flow.

In some variations, passing the endoluminal instrument within the introducer device to a first instrument insertion depth 200 may include positioning the endoluminal instrument at least partially based on a visual reference on the introducer device. As described above with respect to some variations of the introducer device, in some variations the visual reference may be indicated by a reference line marked on the internal and/or external surface of the introducer device (e.g., a decal or etched line). The visual reference for the first instrument insertion depth may, for example, include any of the variations described above with respect to variations of the introducer device.

Advancing the introducer device toward the target region of the body cavity 220 positions the combination of the introducer device and endoluminal instrument closer to an area of interest (e.g., anastomosis) for examination or other purposes. Some of the advancement (e.g., an initial distance) may be performed under direct vision, while some of the advancement may be visualized via the endoluminal instrument itself, such as through a camera in an endoscope. During such advancement toward the target region of the body cavity, the endoluminal instrument in its recessed position at the first instrument insertion depth may remain relatively protected against oncoming debris and other contamination. For instance, in the exemplary arrangement shown in FIGS. 5A and 5B, the endoluminal instrument 10 may be protected by at least the distal segment of the introducer device including the internal projections 130 in the channel 120.

Advancing the endoluminal instrument within the introducer device to a second instrument insertion depth 230 positions the endoluminal instrument at a more distal location within the introducer device and closer to the target region of the body cavity. An exemplary first instrument insertion depth is shown in FIGS. 6A and 6B, where the endoluminal instrument 10 is located at second instrument insertion depth reference 116. At this second location, the endoluminal instrument is moved closer to the target region (e.g., anastomosis) for examination or other purposes. In some variations, the second instrument insertion depth reference may be located proximal to the distal end of the tubular introducer (e.g., about 1 cm to about 2 cm proximal to the distal end of the tubular member) such that the tubular member may protrude distally beyond the end of the endoluminal instrument. This additional length of the tubular member may provide some protection for the endoluminal instrument while not interfering with the field of view for the endoluminal instrument. The second instrument insertion depth reference may include tactile feedback and/or visual reference, similar to the first instrument insertion depth reference.

After advancing the endoluminal instrument to the second instrument insertion depth, the endoluminal instrument may be operated near the target region (e.g., anastomosis). For instance, the endoluminal instrument may illuminate the target region with illumination light and obtain white light images of the target region. As another example, after a fluorescence imaging agent (e.g., indocyanine green, or ICG) is administered to the subject, the endoluminal instrument may direct excitation light toward the target region and capture fluorescence images for assessing blood flow and/or perfusion near the target region. Other steps may be performed as necessary or desired depending on other functionality of the endoluminal instrument (e.g., optical coherence imaging, spectroscopy, tissue sampling, etc.).

After examination and/or other operational steps of the endoluminal instrument are performed, the user may withdraw the introducer device from the body cavity. The endoluminal instrument may be withdrawn from the introducer device while the introducer device remains in the body cavity, or the endoluminal instrument may be withdrawn simultaneously with the introducer device from the body cavity.

Other Variations

In some variations, as shown in FIGS. 8A-8D, the introducer 800 may be composed of a rigid plastic formed into a tube structure by molding, extrusion or other appropriate plastic manufacturing process. The plastic may be selected from a medical plastic, polypropylene, polycarbonate, polyethylene, polystyrene, K-resin, or any other appropriate rigid plastic. The tube structure may be transparent or opaque. The introducer may contain a single main channel or a main channel with one or more ancillary channels 802—the laparoscope being inserted into a main channel and the other channels being utilized for insufflation, washing and aspiration of fluids from the endoluminal surface. If the introducer has a single main channel that is open to the endoluminal space, then the space between the laparoscope and the tube wall may be utilized for insufflation, washing and aspiration of fluids from the endoluminal surface.

In many embodiments, the introducer may be approximately the length of the laparoscope 850, such that when the laparoscope is inserted into the introducer, the tip of the endoscope reaches, but does not protrude from the end of the introducer. The main channel 803 of the introducer may be sealed at the distal end with a transparent window 804 and, if sealed, the main channel window may be transparent to UV, visible or near infra-red light. The tip of the laparoscope may be sufficiently close to the end of the main channel of the introducer, so that the introducer does not enter the field of view seen through the laparoscope or block the illumination emitted by laparoscope.

The tip of the introducer may be angled at a suitable angle (e.g., 30°, 45°, or 90°) to accommodate angle viewing laparoscopes. Ancillary channels for washing and aspiration may be appropriately directed to terminate in the same direction as the viewing angle. A separate ancillary channel may be terminated to direct a spray of wash water across the window of the main channel.

The tip of the introducer may be composed of a softer more compliant plastic than the remainder of the shaft of the introducer, (e.g., Teflon or a similar material) or may have rounded edges so as not to scrape the endoluminal surface when inserted.

As shown in FIG. 8B, the introducer may have markings 806 on the exterior surface to indicate the depth of insertion.

As shown in FIGS. 8B and 8D, the proximal end of the introducer may have a feature 810 that seats the laparoscope light guide stem and maintains it in position such that the introducer and laparoscope will move together if rotated. This is especially useful in instances when side-viewing laparoscopes are used.

The proximal end of the introducer may have a connection point for the insufflation, aspiration and/or washing channel(s) such as a luer connection or a hose barb. An insufflation bulb can be connected to the insufflation connection point 801. Alternatively, other insufflation sources (such as pumps, plumbed pressurized gas, etc.) may be connected to the insufflation connection point. This allows for greater flexibility in choice of insufflation apparatus and also allows for replacement of the insufflation apparatus without necessitating replacement of the entire introducer.

In some variations as shown in FIG. 9A, the proximal end of the introducer may contain a number of valves 912 for controlling the insufflation, aspiration, and/or wash functions of the introducer. One possible arrangement of separate channels and valves for this purpose, but in no way intended to be limiting, is shown in FIGS. 9A and 9B. Insufflation air and wash water may be supplied by an air pump and water bottle built into the endoscopic illuminator or as standalone components. Alternatively, plumbed-in air or CO2, water and vacuum lines in the operating room may be used. Aspiration may be provided by a vacuum pump or similar vacuum source.

As shown in FIG. 9A, the proximal end of the introducer may also have a flange or tabs or handle 911 that facilitates easier handling of the laparoscope and introducer assembly. This handle may also contain a number of valves for controlling the insufflation, suction and wash functions of the introducer. The valves may be deployed in any arrangement that allows for separate and reliable control of the insufflation, wash and aspiration functions. The handle may be positioned at an angle to the main structure of the introducer so that it can be manipulated and operated in a gun fashion.

As shown in FIGS. 10A and 10B, in some variations, the main channel at the distal end of the introducer may lack a window that seals and separates the endoscope from the endoluminal space. In these variations, the laparoscope tip may be exposed to the endoluminal surface and the introducer may contain a circumferential seal 1008 between the exterior of the laparoscope and the interior surface of the main channel of the introducer so as to contain the insufflation air within the endoluminal cavity. The seal may be located anywhere along the length of the introducer main channel containing the laparoscope shaft. The seal may be composed of rubber, silicon or other compliant and sufficiently impermeable material. The seal may be in the form of a valve, a wiping seal, 2-stage seal (e.g., a cross slit valve and backup seal) or compliant compression seal (e.g., an O-ring). Such an embodiment may also integrate the insufflation and main channels of the introducer into a single channel. Such an embodiment may also integrate one or more separate ancillary channels to direct a spray of wash water across the tip of the laparoscope or ancillary channels for the irrigation and aspiration of fluids.

In some variations, as shown in FIGS. 11A-11E, the introducer may feature a connection mechanism at some point between the distal and proximal ends such that the device may be assembled prior to insertion of the laparoscope. The connection may be in the form of a threaded connection 1113c as shown in FIGS. 11D and 11E, snap-fit connection 1113a as shown in FIG. 11A, twist & lock or compression connection 1113b as shown in FIGS. 11B and 11C, or other suitable connection. The connection may prevent leaking of insufflation gas and the transfer of any fluids in ancillary channels. The connection may feature a seal of any type described herein or other suitable seal, so as to maintain insufflation pressure in the connection.

Figure 12A:
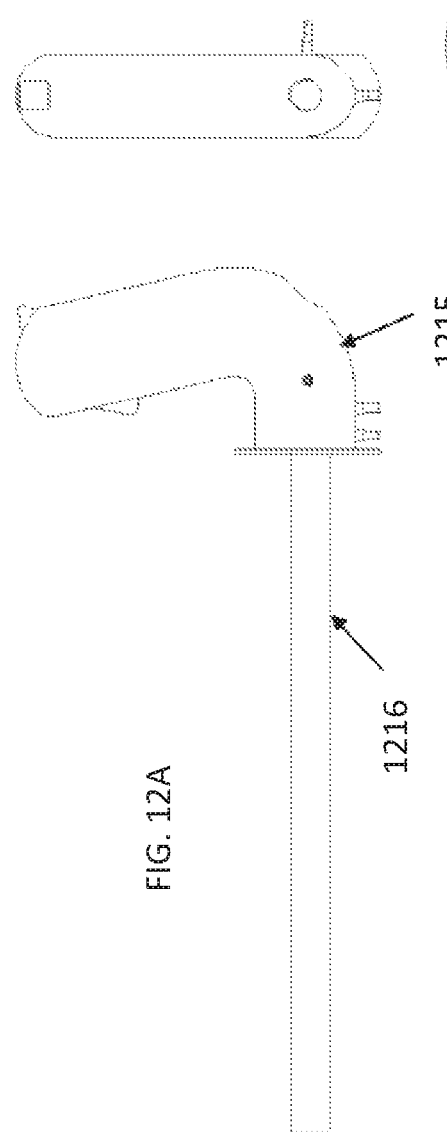
FIGS. 12A-12C depict an exemplary handle in another variation of an introducer device.
Figure 12B:
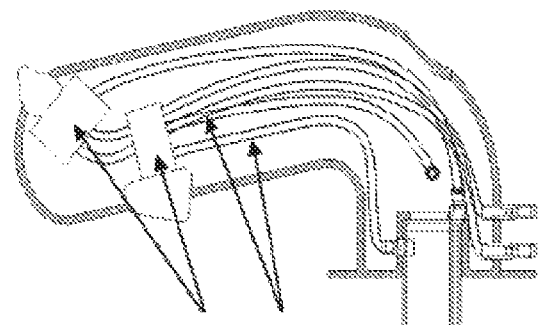
Figure 12C:

In some variations, as shown in FIGS. 12A-12C, the introducer may feature a removable handle extending at any non-parallel angle in relation to the tube axis. This handle may also contain the valves used to control insufflation, wash/irrigation and aspiration functions. In these variations, the handle 1215 may be a reusable component that attaches to a single-use tube 1216 that would be inserted inside the subject. The reusable handle may contain reusable or single-use valves 1217 and fluid channels 1218 that connect to the main and/or ancillary lumens. The handle may be positioned at an angle to the main structure of the introducer so that it can be manipulated and operated in a gun fashion.

A kit may include one or more variations of the introducer device described herein and a fluorescence imaging agent. For example, the fluorescence imaging agent may comprise a fluorescence dye, an analogue thereof, a derivative thereof, or a combination of these. A fluorescence dye may include any non-toxic fluorescence dye. In some variations, the fluorescence imaging agent optimally emits fluorescence in the near-infrared spectrum. In some variations, the fluorescence imaging agent is or comprises a tricarbocyanine dye such as, for example, indocyanine green (ICG). In other variations, the fluorescence imaging agent is or comprises fluorescein isothiocyanate, rhodamine, phycoerythrin, phycocyanin, allophycocyanin, o-phthaldehyde, fluorescamine, rose Bengal, trypan blue, fluoro-gold, green fluorescence protein, flavins (e.g., riboflavin, etc.), methylene blue, porphysomes, cyanine dyes (e.g., cathepsin-activated Cy5 combined with a targeting ligand, Cy5.5, etc.), IRDye800CW, CLR 1502 combined with a targeting ligand, OTL38 combined with a targeting ligand, or a combination thereof, which is excitable using excitation light wavelengths appropriate to each imaging agent. In some variations, an analogue or a derivative of the fluorescence imaging agent may be used. For example, a fluorescence dye analogue or a derivative may include a fluorescence dye that has been chemically modified, but still retains its ability to fluoresce when exposed to light energy of an appropriate wavelength. In variations where some or all of the fluorescence is derived from autofluorescence, one or more of the fluorophores giving rise to the autofluorescence may be an endogenous tissue fluorophore (e.g., collagen, elastin, NADH, etc.), 5-aminolevulinic Acid (5-ALA), or a combination thereof. In another aspect, the kit may include an endoscope (e.g., laparoscope, sigmoidoscope, proctoscope, rectoscope, colonoscope, etc.). For example, the endoscope may include a camera or other imaging system for white light imaging, fluorescence imaging, spectral imaging, infrared imaging, optical coherence imaging, and/or other suitable imaging modalities. In yet further aspects, the kit may include instructions for use. The instructions for use may, for example, describe generally one or more variations of the method for using the introducer device as described herein.

While the invention has been described in the context of examination of an anastomosis or surgical margin in the rectum of a subject following LAR surgery, it will be readily apparent to those of skill in the art that the introducer device of the present invention could be used in other contexts. For example, alternate embodiments of the introducer device could be deployed in other proximal regions of the bowel or in other body orifices where it would be advantageous to have an introducer device that provides multiple channels for imaging and other functionalities (such as irrigation and aspiration) and that provides protection for the surrounding tissue from the surfaces of the laparoscope. As has been described herein in the context of LAR surgery, one or more variations of the introducer could be used in conjunction with a conventional, white-light laparoscope or with an endoscope capable of near infra-red fluorescence illumination and imaging, or with any suitable endoscope or other endoluminal instrument.

While the endoluminal introducer device and methods for using an endoluminal introducer device have been illustrated and described in connection with the variations shown and described in detail, it is not intended to be limited to the details herein and in the figures, since various modifications and structural changes may be made without departing in any way from the scope of the present invention. Other variations of the endoluminal introducer device include any suitable combination of any set or subset of features described in one or more of the above-described and illustrated variations. Similarly, other variations of the methods for using an introducer device include any suitable combination of set or subset of steps described in one or more of the above-described and illustrated variations. The embodiments chosen and described explain the principles of the invention and its practical application and do thereby enable a person of skill in the art to best utilize the invention and its various embodiments.

What is claimed is:

1. An introducer device for a solid endoluminal instrument, the introducer device comprising:
    a tubular member having an inner wall that defines a channel configured to receive at least a portion of the endoluminal instrument;
    an insufflation port coupled to the tubular member and configured to pass insufflation gas into the channel; and
    a plurality of projections disposed in the channel at circumferentially spaced apart locations around the inner wall;
    wherein the projections extend inward and are configured to offset the endoluminal instrument from the inner wall, thereby creating a space between the endoluminal instrument and the inner wall.

2. The introducer device of claim 1, wherein the projections are disposed in a distal segment of the channel.

3. The introducer device of claim 1, wherein a distal end of the channel is in fluid communication with the space between the endoluminal instrument and the inner wall.

4. The introducer device of claim 1, wherein the projections are approximately radially symmetrically arranged around the inner wall.

5. The introducer device of claim 1, wherein at least one projection includes a longitudinal ridge extending along the channel.

6. The introducer device of claim 5, wherein the longitudinal ridge is of approximately uniform height along its longitudinal axis.

7. The introducer device of claim 5, wherein at least a portion of the longitudinal ridge is sloped along its longitudinal axis.

8. The introducer device of claim 5, wherein a distal endpoint of the longitudinal ridge is located proximal to the distal end of the tubular member.

9. The introducer device of claim 5, wherein the projections include at least four longitudinal ridges equally distributed around the inner wall.

10. The introducer device of claim 1, wherein at least one projection includes an approximately round bump.

11. The introducer device of claim 1, wherein the tubular member defines a first instrument insertion depth reference that indicates a first position for the endoluminal instrument relative to the tubular member, and a second instrument insertion depth reference that indicates a second position for the endoluminal instrument relative to the tubular member.

12. The introducer device of claim 11, wherein at least one of the first and second instrument insertion depth references includes tactile feedback resulting from interference between at least one of the projections and the endoluminal instrument.

13. The introducer device of claim 11, wherein at least one of the first and second instrument insertion depth references includes a visual reference on the tubular member.

14. The introducer device of claim 13, wherein the visual reference includes a reference line.

15. The introducer device of claim 1, wherein the projections are integrally formed with the inner wall.

16. A kit for facilitating the passage of an endoluminal instrument to a target region of a body cavity, comprising the introducer device of claim 1 and a fluorescence imaging agent.

17. A method for using an introducer device to facilitate passing a solid endoluminal instrument to a target region of a body cavity, the method comprising:
    passing the endoluminal instrument within a channel defined by an inner wall of a tubular member of the introducer device to a first instrument insertion depth, wherein the introducer device comprises an insufflation port coupled to the tubular member and configured to pass insufflation gas into the channel;
    advancing the introducer device toward the target region of the body cavity while the endoluminal instrument is positioned within the introducer device at the first instrument insertion depth; and
    advancing the endoluminal instrument within the introducer device to a second instrument insertion depth that is distal to the first instrument insertion depth, wherein when the endoluminal introducer is at the second instrument insertion depth there is a space between the endoluminal instrument and the inner wall of the introducer device, wherein the introducer device comprises a plurality of projections disposed in the channel at circumferentially spaced apart locations around the inner wall that extend inward and are configured to offset the endoluminal instrument from the inner wall, thereby creating the space between the endoluminal instrument and the inner wall.

18. The method of claim 17, wherein advancing the endoluminal instrument includes centering the endoluminal instrument within the introducer device.

19. The method of claim 17, wherein passing the endoluminal instrument within the introducer device to a first instrument insertion depth includes positioning the endoluminal instrument at least partially based on tactile feedback resulting from interference between the endoluminal instrument and an internal projection of the introducer device.

20. The method of claim 17, wherein passing the endoluminal instrument within the introducer device to a first instrument insertion depth includes positioning the endoluminal instrument at least partially based on a visual reference on the introducer device.

21. The method of claim 17, wherein advancing the endoluminal instrument within the introducer device to a second instrument insertion depth includes positioning the endoluminal instrument at least partially based on a visual reference on the introducer device.

* * * * *